(12) United States Patent
Bolduc et al.

(10) Patent No.: US 8,680,233 B2
(45) Date of Patent: Mar. 25, 2014

(54) HETEROPEPTIDES USEFUL FOR REDUCING NONSPECIFIC ADSORPTION

(75) Inventors: Olivier Bolduc, Laval (CA); Joelle N. Pelletier, Ville Mont-Royal (CA); Jean-Francois Masson, Montreal (CA)

(73) Assignee: Valorisation-Recherche, Limited Partnership, Montreal (CA)

(*) Notice: Subject to any disclaimer, the term of this patent is extended or adjusted under 35 U.S.C. 154(b) by 0 days.

(21) Appl. No.: 13/510,163

(22) PCT Filed: Nov. 16, 2010

(86) PCT No.: PCT/CA2010/001778
§ 371 (c)(1),
(2), (4) Date: May 16, 2012

(87) PCT Pub. No.: WO2011/060528
PCT Pub. Date: May 26, 2011

(65) Prior Publication Data
US 2012/0329986 A1    Dec. 27, 2012

Related U.S. Application Data

(60) Provisional application No. 61/261,915, filed on Nov. 17, 2009.

(51) Int. Cl.
| A61K 38/00 | (2006.01) |
| A61K 39/00 | (2006.01) |
| C07K 14/47 | (2006.01) |
| C07K 7/06 | (2006.01) |
| B01J 20/28 | (2006.01) |
| C07K 17/00 | (2006.01) |
| C08G 69/10 | (2006.01) |
| C40B 30/04 | (2006.01) |
| C40B 40/10 | (2006.01) |
| C40B 50/18 | (2006.01) |
| G01N 33/50 | (2006.01) |

(52) U.S. Cl.
USPC .................. 530/300; 530/329; 530/330

(58) Field of Classification Search
CPC ....... A61K 38/00; A61K 39/00; C07K 14/47; C07K 7/06
USPC .......................... 530/300, 329, 330
See application file for complete search history.

(56) References Cited

U.S. PATENT DOCUMENTS

| 5,866,683 | A * | 2/1999 | Shimura et al. ............... 530/328 |
| 6,159,722 | A * | 12/2000 | Bode et al. ..................... 435/219 |
| 6,372,720 | B1 * | 4/2002 | Longmuir et al. .......... 514/44 R |
| 6,660,492 | B1 | 12/2003 | Bode et al. |
| 7,090,973 | B1 * | 8/2006 | Breton ........................ 435/6.19 |
| 7,179,784 | B2 | 2/2007 | Zhang et al. |
| 7,348,408 | B2 * | 3/2008 | Gokce et al. .................. 530/350 |
| 7,504,490 | B1 | 3/2009 | Weinstock et al. |
| 7,534,761 | B1 | 5/2009 | Stupp et al. |
| 2003/0119018 | A1 * | 6/2003 | Omura et al. ..................... 435/6 |
| 2003/0176335 | A1 * | 9/2003 | Zhang et al. ..................... 514/12 |
| 2003/0228280 | A1 * | 12/2003 | Graham et al. ............. 424/93.2 |
| 2004/0010134 | A1 * | 1/2004 | Rosen et al. ................. 536/23.5 |
| 2004/0235721 | A1 * | 11/2004 | Weber et al. ..................... 514/12 |
| 2007/0042392 | A1 * | 2/2007 | Tang et al. ......................... 435/6 |
| 2007/0061916 | A1 * | 3/2007 | Kovalic et al. ................ 800/278 |
| 2007/0271633 | A9 * | 11/2007 | Kovalic et al. ................ 800/284 |
| 2008/0009077 | A1 * | 1/2008 | Matsuo et al. ................ 436/501 |

FOREIGN PATENT DOCUMENTS

| JP | 2009261388 | 11/2009 |
| WO | WO02057780 | 7/2002 |
| WO | WO2004003561 | 1/2004 |
| WO | WO2009023270 | 2/2009 |
| WO | WO 2009023270 A2 * | 2/2009 |

OTHER PUBLICATIONS

ISR and WO, Feb. 4, 2011, PCT/CA2010/001778.
Baca et al., "Chemical Ligation of Cysteine-Containing Peptides: Synthesis of a 22 kDA Tethered Dimer of HIV-1 Protease", J. Am. Chem. Soc. 117: 1881-1887, 1995.
Blankespoor, R. et al., "Dense Monolayers of Metal-Chelating Ligands Covalently Attached to Carbon Electrodes Electrochemically and Their Useful Application in Affinity Binding of Histidine-Tagged Proteins", 2005. Langmuir 21(8), 3362-3375.
Bolduc, O. R. and Masson, J. F., "Monolayers of 3-Mercaptopropyl-amino Acid to Reduce the Nonspecific Absorption of Serum Proteins on the Surface of Biosensors", Langmuir 2008, 24: 12085.
Bolduc, O. R. et al., "Peptide Self-Assembled Monolayers for Label-Free and Unamplified Surface Plasmon Resonance Biosensing in Crude Cell Lysate" Anal. Chem. 2009, 81: 6779.
Dostalek, J. et al., "SPR Biosensors for Detection of Biological and Chemical Analytes", Springer Ser Chem Sens Biosens 2006, 4:177-190.
Duevel, R.V., Corn, R.M., "Amide and Ester Surface Attachment Reactions for Alkanethiol Monolayers at Gold Surfaces As Studies by Polarization Modulation Fourier Transform Infrared Spectroscopy", 1992. Analytical Chemistry 64(4), 337-342.
Eisenberg et al., "Analysis of Membrane and Surface Protein Sequences with the Hydrophobic Moment Plot", J. Mol. Biol. 179: 125-142, 1984).
Furuya, M. et al., "Reduction of nonspecific binding proteins to self-assembled monolayer on gold surface", Biorg. Med. Chem. 2006, 14: 537.
Green, R. J. et al., "Surface plasmon resonance for real time in situ analysis of protein adsorption to polymer surfaces", Biomaterials 1997, 18: 405.
Green, R. J. et al., "Competitive protein adsorption as observed by surface plasmon surface", Biomaterials 1999, 20: 385.

(Continued)

*Primary Examiner* — Christina Bradley
*Assistant Examiner* — Kristina M Hellman
(74) *Attorney, Agent, or Firm* — Goudreau Gage Dubuc; S. Serge Shahinian; Alain Dumont

(57) ABSTRACT

Reagents, kits, uses and methods useful for example for decreasing nonspecific adsorption of biomolecules at the surface of a solid support are disclosed. Such reagents and methods, which are based on short heteropeptides, may be used to decrease nonspecific adsorption in for example biosensing applications.

12 Claims, 12 Drawing Sheets

(56) References Cited

OTHER PUBLICATIONS

Homola, J. et al., "Surface plasmon resonance sensors: review", Sensors and Actuators B-Chemical 1999, 54: 3.

Homola, J. "Present and future of surface plasmon resonance biosensors", Anal Bioanal Chem (2003) 377 : 528-539.

Keller, T.A. et al., "Reversible oriented immobilization of histidine-tagged proteins on gold surfaces using a chelator thioalkane", 1995. Supramolecular Science 2(3-4), 155-160.

Kröger, D. et al., "Immobilization of histidine-tagged proteins on gold surfaces using chelator thioalkanes", 1999. Biosensors and Bioelectronics 14(2), 155-161.

Liu et al., "Acyl disulfide-mediated intramolecular acylation for orthogonal coupling between unprotected peptide segments, mechanism and application", Tetrahedron Lett. 37: 933-936, 1996.

Liu and Tam, " Chemical litigation approach to form a peptide bond between unprotected peptide segments concept and model study", J. Am. Chem. Soc. 116: 4149-4153, 1994.

Liu and Tam, "Peptide segment ligation strategy without use of protecting groups", Proc. Natl. Acad. Sci. USA 91: 6584-6588, 1994.

Luppa, P. B. et al., "Immunosensors—principles and applications to clinical chemistry", Clin. Chim. Acta 2001, 314: 1.

Masson, J. F. et al., "Reduction of nonspecific protein binding on surface plasmon resonance biosensors", Anal. Bioanal. Chem. 2006, 386: 1951-1959.

Masson, J. F. et al., "Biocompatible polymers for antibody support on gold surfaces", Talanta 2005, 67: 918-925.

Morimoto, N. et al., "Physical properties and blood compatibility of surface-modified segmented polyurethane by semi-interpenetrating polymer networks with a phospholipid polymer", Biomaterials 2002, 23: 4881.

Nakagawa et al., "The use of polymer-bound oximes for the synthesis of large peptides usable in segment condensation: synthesis of a 44 amino acid amphiphilic peptide model of apolipoprotein A-1", J. Am. Chem. Soc. 107: 7087-7092, 1985.

Phillips, K. and Cheng, "Recent advances in surface plasmon resonance based techniques for bioanalysis", Q. Anal. Bioanal. Chem. 2007, 387: 1831.

Porfirieva, A. et al., "Polyphenothiazine modified electrochemical aptasensor for detection of human a-thrombin", Electroanalysis 2007, 19: 1915-1920.

Rich, R. L. and Myszka, D. G., "Advances in surface plasmon resonance biosensor analysis", Curr. Opin. Biotechnol. 2000, 11: 54-61.

Sakurai, T. et al., "Formation of oriented polypeptides on Au(111) surface depends on the secondary structure controlled by peptide length", 2006. Journal of Peptide Science 12(6), 396-402.

Sankaranarayanan, S. K. R. S.; et al., "Flow induced by acoustic streaming on surface-acoustic-wave devices and its application in biofouling removal: A computational study and comparisons to experiment", Physical Review E (Statistical, Nonlinear, and Soft Matter Physics) 2008, 77: 066308.

Schnolzer and Kent, "Contructing proteins by dovetailing unprotected synthetic peptides: backbone-engineered HIV protease", Science 256: 221-225, 1992.

Tam et al., "Specificity and formation of unusual amino acids of an amide ligation strategy for unprotected peptides", Int. J. Peptide Protein Res. 45: 209-216, 1995.

Tinazli, A. et al., "High-affinity chelator thiols for switchable and oriented immobilization of histidine-tagged proteins: a generic platform for protein chip technologies", 2005. Chemistry—A European Journal 11(18), 5249-5259.

Volpato et al., "Increasing methotrexate resistance by combination of active-side mutations in human dihydrofolate reductase", 2007 Journal of Molecular Biology 373, 599-611.

Xu et al., "Combined affinity and catalytic biosensor: in situ enzymatic activity monitoring of surface-bound enzymes", 2005. Journal of the American Chemical Society 127(38), 13084-13085.

Yamashiro and Li, "New segment synthesis of x-inhibin-92 by the acyl disulfide method", Int. J. Peptide Protein Res. 31: 322-334, 1988.

\* cited by examiner

SEQUENCE LISTING

```
<160> NUMBER OF SEQ ID NOS: 59

<210> SEQ ID NO 1
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: The amino terminal is modified with a 3-
      mercaptopropionic acid moiety

<400> SEQUENCE: 1

His His His Asp Asp
1               5

<210> SEQ ID NO 2
<211> LENGTH: 5
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: The amino terminal is modified with a 3-
      mercaptopropionic acid moiety

<400> SEQUENCE: 2

Ser Ser Ser Ser Ser
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: The amino terminal is modified with a 3-
      mercaptopropionic acid moiety

<400> SEQUENCE: 3

His His His His His
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: The amino terminal is modified with a 3-
      mercaptopropionic acid moiety

<400> SEQUENCE: 4

Asp Asp Asp Asp Asp
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: The amino terminal is modified with a 3-
      mercaptopropionic acid moiety

<400> SEQUENCE: 5

Leu Leu Leu Leu Leu
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: The amino terminal is modified with a 3-
      mercaptopropionic acid moiety
```

```
<400> SEQUENCE: 6

Phe Phe Phe Phe Phe
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: The amino terminal is modified with a 3-
      mercaptopropionic acid moiety

<400> SEQUENCE: 7

His His His His Asp
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: The amino terminal is modified with a 3-
      mercaptopropionic acid moiety

<400> SEQUENCE: 8

His His Asp Asp Asp
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: The amino terminal is modified with a 3-
      mercaptopropionic acid moiety

<400> SEQUENCE: 9

His Asp Asp Asp Asp
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic peptide

<400> SEQUENCE: 10

Ser Ser Ser Asp Asp
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic peptide
```

```
<400> SEQUENCE: 11

His His His Asp Asp
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic peptide

<400> SEQUENCE: 12

Leu Leu Leu Asp Asp
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic peptide

<400> SEQUENCE: 13

Leu Leu Leu Ser Ser
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic peptide

<400> SEQUENCE: 14

Leu Leu Leu His His
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic peptide

<400> SEQUENCE: 15

His His His Ser Ser
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic peptide

<400> SEQUENCE: 16

Asp Asp Asp His His
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic peptide

<400> SEQUENCE: 17
```

```
Asp Asp Asp Ser Ser
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic peptide

<400> SEQUENCE: 18

Ser Ser Ser His His
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: The amino terminal is modified with a 3-
      mercaptopropionic acid moiety

<400> SEQUENCE: 19

Ser Ser Ser Asp Asp
1               5

<210> SEQ ID NO 20
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: The amino terminal is modified with a 3-
      mercaptopropionic acid moiety

<400> SEQUENCE: 20

Leu Leu Leu Asp Asp
1               5

<210> SEQ ID NO 21
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: The amino terminal is modified with a 3-
      mercaptopropionic acid moiety

<400> SEQUENCE: 21

Leu Leu Leu Ser Ser
1               5

<210> SEQ ID NO 22
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
```

```
<223> OTHER INFORMATION: The amino terminal is modified with a 3-
      mercaptopropionic acid moiety

<400> SEQUENCE: 22

Leu Leu Leu His His
1               5

<210> SEQ ID NO 23
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: The amino terminal is modified with a 3-
      mercaptopropionic acid moiety

<400> SEQUENCE: 23

His His His Ser Ser
1               5

<210> SEQ ID NO 24
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: The amino terminal is modified with a 3-
      mercaptopropionic acid moiety

<400> SEQUENCE: 24

Asp Asp Asp His His
1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: The amino terminal is modified with a 3-
      mercaptopropionic acid moiety

<400> SEQUENCE: 25

Asp Asp Asp Ser Ser
1               5

<210> SEQ ID NO 26
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: The amino terminal is modified with a 3-
      mercaptopropionic acid moiety

<400> SEQUENCE: 26

Ser Ser Ser His His
1               5
```

```
<210> SEQ ID NO 27
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: The amino terminal is modified with a 3-
      mercaptopropionic acid moiety

<400> SEQUENCE: 27

Asp His Asp His Asp
1               5

<210> SEQ ID NO 28
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: The amino terminal is modified with a 3-
      mercaptopropionic acid moiety

<400> SEQUENCE: 28

Gly Gly Gly Gly Asp
1               5

<210> SEQ ID NO 29
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: The amino terminal is modified with a 3-
      mercaptopropionic acid moiety

<400> SEQUENCE: 29

Leu His Asp Leu His Asp
1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: The amino terminal is modified with a 3-
      mercaptopropionic acid moiety

<400> SEQUENCE: 30

Leu Leu His His Asp Asp
1               5

<210> SEQ ID NO 31
<211> LENGTH: 6
<212> TYPE: PRT
<213> ORGANISM: Artificial Sequence
<220> FEATURE:
<223> OTHER INFORMATION: Synthetic peptide
```

```
<400> SEQUENCE: 31

Gly Gly His His Asp Asp
1               5

<210> SEQ ID NO 32
<211> LENGTH: 5
<212> TYPE: PRT
<213> ORGANISM: Artificial Sequence
<220> FEATURE:
<223> OTHER INFORMATION: Synthetic peptide

<400> SEQUENCE: 32

Asp Ser Asp Ser Asp
1               5

<210> SEQ ID NO 33
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: The amino terminal is modified with a 3-
      mercaptopropionic acid moiety

<400> SEQUENCE: 33

Ser His Asp Ser His Asp
1               5

<210> SEQ ID NO 34
<211> LENGTH: 6
<212> TYPE: PRT
<213> ORGANISM: Artificial Sequence
<220> FEATURE:
<223> OTHER INFORMATION: Synthetic peptide

<400> SEQUENCE: 34

Ser His Asp Ser His Asp
1               5

<210> SEQ ID NO 35
<211> LENGTH: 6
<212> TYPE: PRT
<213> ORGANISM: Artificial Sequence
<220> FEATURE:
<223> OTHER INFORMATION: Synthetic peptide

<400> SEQUENCE: 35

Leu His Asp Leu His Asp
1               5

<210> SEQ ID NO 36
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: The carboxy terminal is modified with a
      nitriloacetic acid- (NTA) based moiety

<400> SEQUENCE: 36

Ser Ser Ser Asp Asp
1               5
```

```
<210> SEQ ID NO 37
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: The carboxy terminal is modified with a
      nitriloacetic acid- (NTA) based moiety

<400> SEQUENCE: 37

His His His Asp Asp
1               5

<210> SEQ ID NO 38
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: The carboxy terminal is modified with a
      nitriloacetic acid- (NTA) based moiety

<400> SEQUENCE: 38

Leu Leu Leu Asp Asp
1               5

<210> SEQ ID NO 39
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: The carboxy terminal is modified with a
      nitriloacetic acid- (NTA) based moiety

<400> SEQUENCE: 39

Leu Leu Leu Ser Ser
1               5

<210> SEQ ID NO 40
<211> LENGTH: 5
<212> TYPE: PRT
<213> ORGANISM: Artificial Sequence
<220> FEATURE:
<223> OTHER INFORMATION: LLLHH
<220> FEATURE:
<221> NAME/KEY: MISC_FEATURE
<222> LOCATION: (5)..(5)
<223> OTHER INFORMATION: The carboxy terminal is modified with a
      nitriloacetic acid- (NTA) based moiety

<400> SEQUENCE: 40

Leu Leu Leu His His
1               5

<210> SEQ ID NO 41
<211> LENGTH: 5
<212> TYPE: PRT
<213> ORGANISM: Artificial Sequence
<220> FEATURE:
<223> OTHER INFORMATION: Synthetic peptide
<220> FEATURE:
```

-continued

```
<221> NAME/KEY: MISC_FEATURE
<222> LOCATION: (5)..(5)
<223> OTHER INFORMATION: The carboxy terminal is modified with a
      nitriloacetic acid- (NTA) based moiety

<400> SEQUENCE: 41

His His His Ser Ser
1               5

<210> SEQ ID NO 42
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: The carboxy terminal is modified with a
      nitriloacetic acid- (NTA) based moiety

<400> SEQUENCE: 42

Asp Asp Asp His His
1               5

<210> SEQ ID NO 43
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: The carboxy terminal is modified with a
      nitriloacetic acid- (NTA) based moiety

<400> SEQUENCE: 43

Asp Asp Asp Ser Ser
1               5

<210> SEQ ID NO 44
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: The carboxy terminal is modified with a
      nitriloacetic acid- (NTA) based moiety

<400> SEQUENCE: 44

Ser Ser Ser His His
1               5

<210> SEQ ID NO 45
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: The carboxy terminal is modified with a
      nitriloacetic acid- (NTA) based moiety

<400> SEQUENCE: 45

Leu His Asp Leu His Asp
```

<210> SEQ ID NO 46
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: The carboxy terminal is modified with a
      nitriloacetic acid- (NTA) based moiety

<400> SEQUENCE: 46

Ser His Asp Ser His Asp
1               5

<210> SEQ ID NO 47
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: The carboxy terminal is modified with a
      nitriloacetic acid- (NTA) based moiety

<400> SEQUENCE: 47

Asp Ser Asp Ser Asp
1               5

<210> SEQ ID NO 48
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: The amino terminal is modified with a
      3-mercaptopropionic acid moiety
<220> FEATURE:
<221> NAME/KEY: MISC_FEATURE
<222> LOCATION: (5)..(5)
<223> OTHER INFORMATION: The carboxy terminal is modified with a
      nitriloacetic acid- (NTA) based moiety

<400> SEQUENCE: 48

Ser Ser Ser Asp Asp
1               5

<210> SEQ ID NO 49
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: The amino terminal is modified with a 3-
      mercaptopropionic acid moiety
<220> FEATURE:
<221> NAME/KEY: MISC_FEATURE
<222> LOCATION: (5)..(5)
<223> OTHER INFORMATION: The carboxy terminal is modified with a
      nitriloacetic acid- (NTA) based moiet

<400> SEQUENCE: 49

His His His Asp Asp
1               5

<210> SEQ ID NO 50
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: The amino terminal is modified with a 3-
      mercaptopropionic acid moiety
<220> FEATURE:
<221> NAME/KEY: MISC_FEATURE
<222> LOCATION: (5)..(5)
<223> OTHER INFORMATION: The carboxy terminal is modified with a
      nitriloacetic acid- (NTA) based moiety

<400> SEQUENCE: 50

Leu Leu Leu Asp Asp
1               5

<210> SEQ ID NO 51
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: The amino terminal is modified with a 3-
      mercaptopropionic acid moiety
<220> FEATURE:
<221> NAME/KEY: MISC_FEATURE
<222> LOCATION: (5)..(5)
<223> OTHER INFORMATION: The carboxy terminal is modified with a
      nitriloacetic acid- (NTA) based moiety

<400> SEQUENCE: 51

Leu Leu Leu Ser Ser
1               5

<210> SEQ ID NO 52
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: The amino terminal is modified with a 3-
      mercaptopropionic acid moiety
<220> FEATURE:
<221> NAME/KEY: MISC_FEATURE
<222> LOCATION: (5)..(5)
<223> OTHER INFORMATION: The carboxy terminal is modified with a
      nitriloacetic acid- (NTA) based moiety

<400> SEQUENCE: 52

Leu Leu Leu His His
1               5

<210> SEQ ID NO 53
<211> LENGTH: 5
<212> TYPE: PRT
<213> ORGANISM: Artificial Sequence
<220> FEATURE:
<223> OTHER INFORMATION: Synthetic peptide

```
-continued

<220> FEATURE:
<221> NAME/KEY: MISC_FEATURE
<222> LOCATION: (1)..(1)
<223> OTHER INFORMATION: The amino terminal is modified with a 3-
      mercaptopropionic acid moiety
<220> FEATURE:
<221> NAME/KEY: MISC_FEATURE
<222> LOCATION: (5)..(5)
<223> OTHER INFORMATION: The carboxy terminal is modified with a
      nitriloacetic acid- (NTA) based moiety

<400> SEQUENCE: 53

His His His Ser Ser
1               5

<210> SEQ ID NO 54
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: The amino terminal is modified with a 3-
      mercaptopropionic acid moiety
<220> FEATURE:
<221> NAME/KEY: MISC_FEATURE
<222> LOCATION: (5)..(5)
<223> OTHER INFORMATION: The carboxy terminal is modified with a
      nitriloacetic acid- (NTA) based moiety

<400> SEQUENCE: 54

Asp Asp Asp His His
1               5

<210> SEQ ID NO 55
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: The amino terminal is modified with a 3-
      mercaptopropionic acid moiety
<220> FEATURE:
<221> NAME/KEY: MISC_FEATURE
<222> LOCATION: (5)..(5)
<223> OTHER INFORMATION: The carboxy terminal is modified with a
      nitriloacetic acid- (NTA) based moiety

<400> SEQUENCE: 55

Asp Asp Asp Ser Ser
1               5

<210> SEQ ID NO 56
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: The amino terminal is modified with a 3-
      mercaptopropionic acid moiety
<220> FEATURE:
<221> NAME/KEY: MISC_FEATURE
<222> LOCATION: (5)..(5)
<223> OTHER INFORMATION: The carboxy terminal is modified with a
      nitriloacetic acid- (NTA) based moiety
```

```
<400> SEQUENCE: 56

Ser Ser Ser His His
1               5

<210> SEQ ID NO 57
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: The amino terminal is modified with a 3-
      mercaptopropionic acid moiety
<220> FEATURE:
<221> NAME/KEY: MISC_FEATURE
<222> LOCATION: (6)..(6)
<223> OTHER INFORMATION: The carboxy terminal is modified with a
      nitriloacetic acid- (NTA) based moiety

<400> SEQUENCE: 57

Leu His Asp Leu His Asp
1               5

<210> SEQ ID NO 58
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: The amino terminal is modified with a 3-
      mercaptopropionic acid moiety
<220> FEATURE:
<221> NAME/KEY: MISC_FEATURE
<222> LOCATION: (6)..(6)
<223> OTHER INFORMATION: The carboxy terminal is modified with a
      nitriloacetic acid- (NTA) based moiety

<400> SEQUENCE: 58

Ser His Asp Ser His Asp
1               5

<210> SEQ ID NO 59
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: The amino terminal is modified with a 3-
      mercaptopropionic acid moiety
<220> FEATURE:
<221> NAME/KEY: MISC_FEATURE
<222> LOCATION: (5)..(5)
<223> OTHER INFORMATION: The carboxy terminal is modified with a
      nitriloacetic acid- (NTA) based moiety

<400> SEQUENCE: 59

Asp Ser Asp Ser Asp
1               5
```

HETEROPEPTIDES USEFUL FOR REDUCING NONSPECIFIC ADSORPTION

This application is a National Entry Application of PCT application no PCT/CA2010/001778 filed on Nov. 16, 2010 and published in English under PCT Article 21(2), which itself claims the benefit of U.S. Provisional Patent Application Ser. No. 61/261,915 filed Nov. 17, 2009. All documents noted above are incorporated herein by reference in their entirety.

TECHNICAL FIELD

The present invention generally relates to products and methods which exhibit lower nonspecific interactions and which may be used in a variety of applications, such as for biomolecule detection and biosensing applications.

Pursuant to 37 C.F.R. 1.821(c), a sequence listing is submitted herewith as an ASCII compliant text file named "12810_439-SeqListing_ST25.txt", created on Jul. 18, 2013 and having a size of ~18 kilobytes. The content of the aforementioned file is hereby incorporated by reference in its entirety.

BACKGROUND ART

Numerous biosensing techniques rely on the measurement of chemical or biological processes occurring on surfaces to detect molecules. In particular, affinity biosensors provide a measurable signal triggered by the binding of a molecule to a surface-immobilized receptor. Multiple physico-chemical phenomena can be utilized to measure molecules with affinity biosensors, such as the change in mass, impedance, current, optical output or wavelength, or a change in refractive index among others (Luppa, P. B. et al., *Clin. Chim. Acta* 2001, 314: 1). The latter is especially interesting in the case of measuring proteins, antibodies or enzymes, as these molecules have a large molecular weight and high refractive index resulting in a sensitive response using a refractive index sensor. To measure this response, surface plasmon resonance (SPR) is a label-free analytical technique that allows real-time measurements of small changes of refractive index caused by the binding of a molecule with a molecular receptor such as DNA, enzymes, or antibodies (Homola, J. *Anal. Bioanal. Chem.* 2003, 377: 528; Homola, J. et al. *Sensors and Actuators B-Chemical* 1999, 54: 3; Phillips, K. and Cheng, Q. *Anal. Bioanal. Chem.* 2007, 387: 1831). The SPR effect occurs when a thin metallic film deposited on a dielectric material is excited in total internal reflection. SPR is sensitive to within 200-300 nm over the metallic surface, usually gold or silver. Thereby, any molecule migrating within this sensing volume with a refractive index different from the solution will cause a change in the SPR response. This results in SPR being sensitive to numerous categories of molecules, such as DNA or proteins. The broad sensitivity to many important classes of molecules makes SPR an interesting bioanalytical technology, but at the same time greatly limits its application with real biological samples due to nonspecific adsorption.

Previous studies have demonstrated the ability of SPR affinity biosensors to efficiently detect or quantify specific biological markers in solutions such as buffers or strongly diluted biological matrices (Rich, R. L. and Myszka, D. G. *Curr. Opin. Biotechnol.* 2000, 11: 54). However, for complex matrices containing high concentrations of proteins that have the potential to interact with the surface of the SPR biosensors, the greater potential for nonspecific responses which can mask the analytical signal has limited the scope of SPR to solutions that are pure or contain few impurities (Green, R. J. et al. *Biomaterials* 1997, 18: 405; Green, R. J. et al. *Biomaterials* 1999, 20: 385). The need to reduce nonspecific interactions in biological matrices is common to many analytical techniques such as electrochemical biosensors (Porfirieva, A. et al. *Electroanalysis* 2007, 19: 1915), surface acoustic wave biosensors (Sankaranarayanan, S. K. R. S.; et al. *Physical Review E (Statistical, Nonlinear, and Soft Matter Physics)* 2008, 77: 066308) or SPR biosensors (Furuya, M. et al. *Biorg. Med. Chem.* 2006, 14: 537). Nonspecific adsorption is also a major cause for prosthesis and implant rejection (Morimoto, N. et al. *Biomaterials* 2002, 23: 4881). Hence, the design of chemical layers capable of protecting the surface of SPR sensors or other surfaces against nonspecific adsorption is an important challenge to overcome for the development of biosensors capable of measuring molecules directly in biological samples and for improved biocompatibility of surfaces. In the case of SPR biosensors, proteins contained in the biological solution are the major source of nonspecific adsorption. Proteins are present in the millimolar range in most biological fluids while the analytes of interest are in the nanomolar range or less.

Most techniques used in detection of biomolecules entail sample preparation techniques, and/or secondary detection schemes, and/or amplification of the analytical response. The workhorse of bioanalysis, ELISA assays, requires all three of the above, leading to lengthy, complex and costly procedures. Hence, a bioanalytical technique capable of reducing or eliminating these steps would greatly benefit the medical diagnostic industry. The inability of bioanalytical sensors to detect analytes at low concentrations found in biological samples and directly (without any sample preparation) in the biological sample remains a challenge.

There is thus a need for improved products, reagents and methods for use in such applications.

The present description refers to a number of documents, the content of which is herein incorporated by reference in their entirety.

SUMMARY OF THE INVENTION

In an aspect, the present invention provides a substrate comprising:
a solid support; and
a heteropeptide attached to said support, said heteropeptide comprising a core of formula I or II

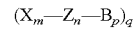  (I)

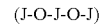  (II)

wherein
X is a domain of m amino acid(s) having similar physico-chemical properties;
Z is a domain of n amino acid(s) having similar physico-chemical properties;
B is a domain of p amino acid(s) having similar physico-chemical properties;
J is an acidic amino acid;
O is a polar amino acid;
m is an integer greater than or equal to 1;
n is an integer greater than or equal to 1;
p is an integer greater than or equal to 0;
q is an integer greater than or equal to 1;
wherein, if p is 0, m+n is an integer greater than or equal to 4; and
wherein the physico-chemical properties of the amino acid(s) of X, Z and B are different (i.e., the physico-chemical properties of X are different from those of Z, the physico-chemical properties of X are different from those of B, and the physico-chemical properties of Z are different from those of B).

In an embodiment, p is 0 and the above-mentioned heteropeptide comprises a core of formula III $$(X_m\text{—}Z_n)_q \tag{III}$$

wherein X is a domain of m amino acid(s) having similar physico-chemical properties; Z is a domain of n amino acid(s) having similar physico-chemical properties; m is an integer greater than or equal to 1; n is an integer greater than or equal to 1; m+n is an integer from greater than or equal to 4; q is an integer ≥1; and wherein the physico-chemical properties of the amino acid(s) of X are different than those of the amino acid(s) of Z. In an embodiment, m is an integer from 1 to 9; n is an integer from 1 to 9; and m+n is an integer from 4 to 10. In a further embodiment, m is an integer from 1 to 4. In yet a further embodiment, m is 3. In an embodiment, n is an integer from 1 to 4. In a further embodiment, n is 2. In an embodiment, m+n is 4, 5 or 6. In a further embodiment, m+n is 5. In an embodiment, q is 1. In an embodiment, the above-mentioned amino acids of X or Z are polar amino acids. In a further embodiment, the above-mentioned polar amino acids are serine (S). In another embodiment, the above-mentioned amino acids of X or Z are basic amino acids. In a further embodiment, the above-mentioned basic amino acids are histidine (H). In another embodiment, the above-mentioned the amino acids of X or Z are acidic amino acids. In a further embodiment, the above-mentioned acidic amino acids are aspartic acid (D). In another embodiment, the above-mentioned amino acids of X are hydrophobic amino acids. In a further embodiment, the above-mentioned hydrophobic amino acids are leucine (L). In an embodiment, the above-mentioned core is SSSDD (SEQ ID NO:10), HHHDD (SEQ ID NO:11), LLLDD (SEQ ID NO:12), LLLSS (SEQ ID NO:13), LLLHH (SEQ ID NO:14), HHHSS (SEQ ID NO:15), DDDHH (SEQ ID NO:16), DDDSS (SEQ ID NO:17) or SSSHH (SEQ ID NO:18).

In an embodiment, p is an integer greater than or equal to 1 and the above-mentioned heteropeptide comprises a core of formula (I)

$$(X_m\text{—}Z_n\text{—}B_p)_q \tag{I}$$

wherein
X is a domain of m amino acid(s) having similar physico-chemical properties;
Z is a domain of n amino acid(s) having similar physico-chemical properties;
B is a domain of p amino acid(s) having similar physico-chemical properties;
m is an integer greater than or equal to 1;
n is an integer greater than or equal to 1;
q is an integer greater than or equal to 1; and
wherein the physico-chemical properties of the amino acid(s) of X, Z and B are different (i.e., the physico-chemical properties of X are different from those of Z, the physico-chemical properties of X are different from those of B, and the physico-chemical properties of Z are different from those of B).

In an embodiment, m is an integer from 1 to 8, in a further embodiment from 1 to 3, in a further embodiment 1; n is an integer from 1 to 8, in a further embodiment from 1 to 3, in a further embodiment 1; p is an integer from 1 to 8, in a further embodiment from 1 to 3, in a further embodiment 1; and m+n+p is an integer from 4 to 10, in a further embodiment 3 or 4, in a further embodiment 3. In an embodiment, m=n=p. In an embodiment, q is 2. In an embodiment, the above-mentioned amino acids of X are polar or hydrophobic amino acids. In a further embodiment, the above-mentioned polar amino acids are serine and the above-mentioned hydrophobic amino acids are leucine (L). In another embodiment, the above-mentioned amino acids of Z are basic amino acids. In a further embodiment, the above-mentioned basic amino acids are histidine (H). In another embodiment, the above-mentioned the amino acids of B are acidic amino acids. In a further embodiment, the above-mentioned acidic amino acids are aspartic acid (D). In an embodiment, the above-mentioned core is LHDLHD (SEQ ID NO:35) or SHDSHD (SEQ ID NO:34).

In an embodiment, the above-mentioned heteropeptide comprises a core of formula (II)

$$(J\text{-}O\text{-}J\text{-}O\text{-}J) \tag{II}$$

wherein
J is an acidic amino acid, in an embodiment aspartic acid (D);
O is a polar amino acid, in an embodiment serine (S);
In an embodiment, the above-mentioned core is DSDSD (SEQ ID NO:32).

In an embodiment, the above-mentioned peptide is attached to said solid support through an N-terminal linker. In a further embodiment, the above-mentioned N-terminal linker is a thiol-containing linker. In a further embodiment, the above-mentioned thiol-containing linker is 3-mercaptoproprionic acid (3-MPA).

In another aspect, the present invention provides a method for reducing nonspecific adsorption on a solid support comprising contacting said solid support with the peptide defined above under conditions permitting binding of said peptide to said support.

In an embodiment, the above-mentioned binding is a covalent binding.

In an embodiment, the above-mentioned solid support is coated with gold.

In another embodiment, the above-mentioned heteropeptide is attached directly to said solid support.

In an embodiment, the above-mentioned solid support is a glass solid support.

In an embodiment, the above-mentioned substrate is a surface plasmon resonance (SPR) biosensor chip.

In another aspect, the present invention provides a heteropeptide of the following formula IV $$R^1\text{—}X^1\text{—}R^2 \tag{IV}$$

wherein
$X^1$ is a peptide core of the amino sequence SSSDD (SEQ ID NO:10), HHHDD (SEQ ID NO:11), LLLDD (SEQ ID NO:12), LLLSS (SEQ ID NO:13), LLLHH (SEQ ID NO:14), HHHSS (SEQ ID NO:15), DDDHH (SEQ ID NO:16), DDDSS (SEQ ID NO:17), SSSHH (SEQ ID NO:18), DSDSD (SEQ ID NO:32), LHDLHD (SEQ ID NO: 35), or SHDSHD (SEQ ID NO: 34).
$R^1$ is a first binding moiety or is absent; and
$R^2$ is a second binding moiety or is absent.

In embodiments, $R^1$ and/or $R^2$ is a reactive or cross-linking moiety. In an embodiment, the above-mentioned $R^1$ is a gold reactive or cross-linking moiety, in a further embodiment a thiol-containing moiety such as 3-mercaptoproprionic acid (3-MPA).

In an embodiment, the above-mentioned $R^2$ is a nitriloacetic acid-(NTA) based moiety. In a further embodiment, the above-mentioned NTA-based moiety is Nα,Nα-bis(carboxymethyl)-L-lysine.

In another embodiment, $R^1$ and $R^2$ are absent.

In another aspect, the present invention provides a method for reducing nonspecific adsorption on a solid support comprising contacting said solid support with the heteropeptide defined above under conditions permitting binding of said heteropeptide to said support.

In another aspect, the present invention provides a kit for reducing the nonspecific adsorption on a solid support, said kit comprising the heteropeptide defined above and instructions for coating a solid support with said peptide. In an embodiment, the above-mentioned kit further comprises one or more reagents for coating said solid support with said peptide.

In an embodiment, the above-mentioned binding or coating is a covalent binding or coating.

In an embodiment, the above-mentioned solid support is coated with gold.

In an embodiment, the above-mentioned solid support is a glass solid support.

In an embodiment, the above-mentioned substrate is a surface plasmon resonance (SPR) biosensor chip.

In another aspect, the present invention provides a method for determining whether a test agent binds to a molecule, said method comprising: (i) providing the substrate defined above comprising the molecule immobilized thereon; (ii) contacting said test agent with said immobilized molecule; (iii) determining whether said test agent binds to said molecule.

In another aspect, the present invention provides a method for determining whether a binding partner or ligand for a molecule is present in a test sample, said method comprising: (i) providing the substrate defined above comprising the molecule immobilized thereon; (ii) contacting said test sample with said immobilized molecule; (iii) determining whether binding to said immobilized molecule has occurred; wherein said binding is indicative that a binding partner or ligand for said molecule is present in said test sample.

In another aspect, the present invention provides a method for determining whether a test agent binds to a molecule, said method comprising: (i) immobilizing said molecule on the substrate defined above; (ii) contacting said test agent with said immobilized molecule; (iii) determining whether said test agent binds to said molecule.

In another aspect, the present invention provides a method for determining whether a binding partner or ligand for a molecule is present in a test sample, said method comprising: (i) immobilizing said molecule on the substrate defined above; (ii) contacting said test sample with said immobilized molecule; (iii) determining whether binding to said immobilized molecule has occurred; wherein said binding is indicative that a binding partner or ligand for said molecule is present in said test sample.

In an embodiment, the above-mentioned substrate is the SPR biosensor chip defined above, and wherein said determining is performed by measuring the surface plasmon resonance (SPR) signal.

In an embodiment, the above-mentioned molecule is a biomolecule, in a further a polypeptide.

Other objects, advantages and features of the present invention will become more apparent upon reading of the following non-restrictive description of specific embodiments thereof, given by way of example only with reference to the accompanying drawings.

BRIEF DESCRIPTION OF DRAWINGS

In the appended drawings:

FIG. 8A depicts the measured SPR signal (λSPR/nm) and FIG. 8B depicts the variation in the SPR signal (ΔλSPR/nm);

DISCLOSURE OF INVENTION

Figure 1A:
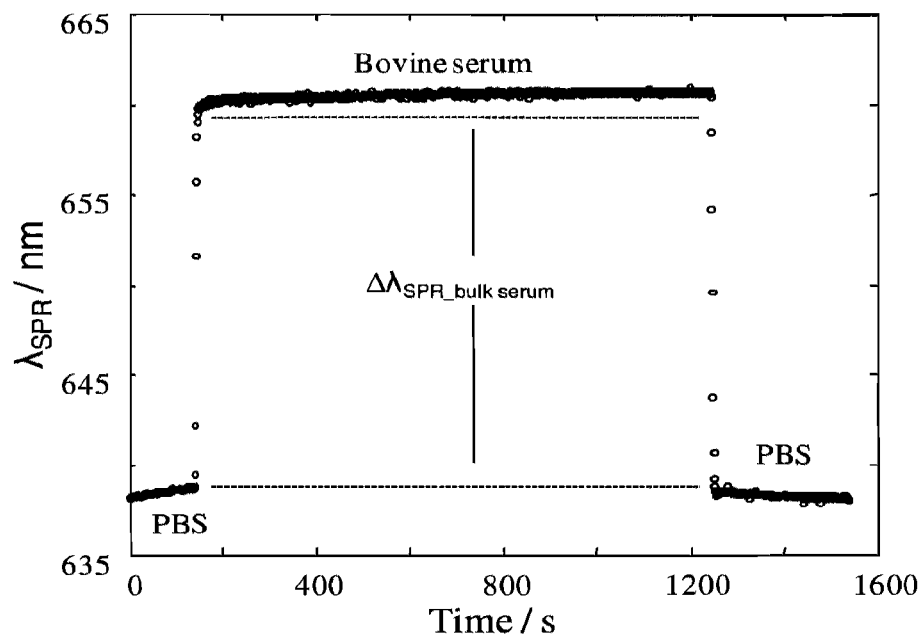
FIG. 1A shows a sensorgram demonstrating the nonspecific adsorption of bovine serum proteins on a self-assembled monolayer (SAM) of 3-MPA-HHHDD-OH (SEQ ID NO:1)

In the studies described herein, the present inventors have shown that the coating of short heteropeptides, and more particularly heteropeptides comprising a core of the formula (I) and (II) described below, on the surface of a biosensor solid support permits to significantly decrease the nonspecific adsorption of biomolecules when using complex matrices such as undiluted serum.

Accordingly, in a first aspect, the present invention provides a substrate (e.g., a biosensor chip) comprising
a solid support; and
a heteropeptide attached to said support, said heteropeptide comprising a core of formula I or II

(I)

(II)

wherein X is a domain of m amino acid(s) having similar physico-chemical properties; Z is a domain of n amino acid(s) having similar physico-chemical properties; B is a domain of p amino acid(s) having similar physico-chemical properties; J is an acidic amino acid; O is a polar amino acid; m is an integer greater than or equal to 1; n is an integer greater than or equal to 1; p is an integer greater than or equal to 0; q is an integer greater than or equal to 1; wherein, if p is 0, m+n is an integer greater than or equal to 4; and wherein the physico-chemical properties of the amino acid(s) of X, Z and B are different.

In an embodiment, the above-mentioned substrate is a low fouling substrate.

In an embodiment, the heteropeptide comprises a core of formula I:

(I)

wherein X is a domain of m amino acid(s) having similar physico-chemical properties; Z is a domain of n amino acid(s) having similar physico-chemical properties; B is a domain of p amino acid(s) having similar physico-chemical properties; m is an integer greater than or equal to 1; n is an integer greater than or equal to 1; p is an integer greater than or equal to 0; q is an integer greater than or equal to 1; wherein, if p is 0, m+n is an integer greater than or equal to 4; and wherein the physico-chemical properties of the amino acid(s) of X, Z and B are different.

In another embodiment, the heteropeptide comprises a core of formula II:

(II)

wherein J is an acidic amino acid; 0 is a polar amino acid and q is an integer greater than or equal to 1;

In an embodiment, the heteropeptide comprises a core of formula III

(III)

wherein
X is a domain of m amino acid(s) having similar physico-chemical properties;
Z is a domain of n amino acid(s) having similar physico-chemical properties;
m is an integer greater than or equal to 1;
n is an integer greater than or equal to 1;
m+n is an integer greater than or equal to 4;
q is an integer greater than or equal to 1; and
wherein the physico-chemical properties of the amino acid(s) of X are different than those of the amino acid(s) of Z.

In an embodiment, m is an integer from 1 to 9 (i.e., 1, 2, 3, 4, 5, 6, 7, 8 or 9), in a further embodiment 1, 2, 3 or 4, and in a further embodiment 2 or 3.

In an embodiment, n is an integer from 1 to 9 (i.e., 1, 2, 3, 4, 5, 6, 7, 8 or 9), in a further embodiment 1, 2, 3 or 4, and in a further embodiment 2 or 3.

In an embodiment, p is an integer from 0 to 8 (i.e., 0, 1, 2, 3, 4, 5, 6, 7 or 8), in a further embodiment 0, 1, 2, 3 or 4, and in a further embodiment 1 or 2.

In an embodiment, if p is 0, m+n is an integer from 4 to 10 (i.e., 4, 5, 6, 7, 8, 9 or 10), in a further embodiment 4, 5 or 6, in a further embodiment 5.

In an embodiment, m+n+p is an integer from 3 to 10 (i.e., 3, 4, 5, 6, 7, 8, 9 or 10), in a further embodiment 3, 4, 5 or 6, in a further embodiment 3 or 6.

In an embodiment, q is 1 or 2.

The term "heteropeptide" as used herein refers to a peptide comprising at least two different amino acids, preferably at least two amino acids having different physico-chemical properties. The term "amino acid" as used herein includes both L- and D-isomers of the naturally occurring amino acids as well as other amino acids (e.g., naturally-occurring amino acids, non-naturally-occurring amino acids, amino acids which are not encoded by nucleic acid sequences, etc.) used in peptide chemistry to prepare synthetic analogs of peptides. Examples of naturally-occurring amino acids are glycine, alanine, valine, leucine, isoleucine, serine, threonine, etc.

Other amino acids include for example norleucine, norvaline, cyclohexyl alanine, biphenyl alanine, homophenyl alanine, naphthyl alanine, pyridyl alanine, phenyl alanines substituted at the ortho, para and meta positions with alkoxy, halogen or nitro groups etc. These amino acids are well known in the art of biochemistry/peptide chemistry. In an embodiment, the above-mentioned heteropeptide comprises naturally-occurring amino acids.

Naturally-occurring amino acids may be classified in four major groups based on their physico-chemical properties. The first group comprises the hydrophobic amino acids which are amino acids exhibiting a hydrophobicity of greater than zero based on the normalized consensus hydrophobicity scale of Eisenberg et al. (*J. Mol. Biol.* 179: 125-142, 1984). Hydrophobic amino acids include leucine (Leu or L), alanine (Ala or A), valine (Val or V), isoleucine (Ile or I), methionine (Met or M), phenylalanine (Phe or F), glycine (Gly or G), tryptophan (Trp or W) and proline (Pro or P). The second group comprises polar, neutral amino acids which are hydrophilic amino acids with a side chain that is uncharged at physiological pH, but which has one bond in which the pair of electrons shared in common by two atoms is held more closely by one of the atoms. Polar amino acids include serine (Ser or S), threonine (Thr or T), cysteine (Cys or C), asparagine (Asn or N), glutamine (Gln or Q) and tyrosine (Tyr or Y). The third group comprises basic amino acids which are hydrophilic amino acids, which typically have positively charged side chains at physiological pH. Basic amino acids include arginine (Arg or R), lysine (Lys or K), and histidine (His or H). Finally, the fourth group comprises acidic amino acids which are hydrophilic amino acids, which typically have negatively charged side chains at physiological pH. Acidic amino acids include aspartic acid and glutamic acid.

Therefore, the expression "amino acids having similar physico-chemical properties" is used herein to refer to naturally-occurring amino acids that belong to the same group, as well as to non-naturally occurring amino acids having physico-chemical properties which are similar to those of naturally-occurring amino acids belonging to the group. Therefore, a domain of 3 amino acid(s) having similar physico-chemical properties may comprise 3 hydrophobic amino acids (identical or different) such as LLL, LAV or MFG. In an embodiment, the above-mentioned domain X comprises identical amino acids. In another embodiment, the above-mentioned domain Z comprises identical amino acids. In another embodiment, the above-mentioned domain B comprises identical amino acids.

In an embodiment, the above-mentioned amino acids of X or Z are polar amino acids, in a further embodiment serine (Ser or S). In another embodiment, the above-mentioned amino acids of X or Z are basic amino acids, in a further embodiment histidine (His or H). In another embodiment, the above-mentioned amino acids of X or Z are acidic amino acids, in a further embodiment aspartic acid (Asp or D). In another embodiment, the above-mentioned amino acids of X are hydrophobic amino acids, in a further embodiment leucine (Leu or L). In an embodiment, the above-mentioned amino acids of B are acidic amino acids; in a further embodiment aspartic acid (Asp or D). In an embodiment, J is an aspartic acid (D). In an embodiment, O is a serine (S).

The above-mentioned heteropeptide or domain may be modified by conservative amino acid changes. Conservative amino acid changes can include the substitution of an L-amino acid by the corresponding D-amino acid, by a conservative D-amino acid, or by a naturally-occurring, non-genetically encoded form of amino acid, as well as a conservative substitution of an L-amino acid. Naturally-occurring non-genetically encoded amino acids include beta-alanine, 3-amino-propionic acid, 2,3-diamino propionic acid, alpha-aminoisobutyric acid, 4-amino-butyric acid, N-methylglycine (sarcosine), hydroxyproline, ornithine, citrulline, t-butylalanine, t-butylglycine, N-methylisoleucine, phenylglycine, cyclohexylalanine, norleucine, norvaline, 2-naphthylalanine, pyridylalanine, 3-benzothienyl alanine, 4-chlorophenylalanine, 2-fluorophenylalanine, 3-fluorophenylalanine, 4-fluorophenylalanine, penicillamine, 1,2,3,4-tetrahydro-isoquinoline-3-carboxylix acid, beta-2-thienylalanine, methionine sulfoxide, homoarginine, N-acetyl lysine, 2-amino butyric acid, 2-amino butyric acid, 2,4-diamino butyric acid, p-aminophenylalanine, N-methylvaline, homocysteine, homoserine, cysteic acid, epsilon-amino hexanoic acid, delta-amino valeric acid, or 2,3-diaminobutyric acid.

In an embodiment, the above-mentioned core comprises from 4 to 10 amino acids. In a further embodiment, the above-mentioned core comprises from 4 to 9 amino acids. In a further embodiment, the above-mentioned core comprises from 4 to 8 amino acids. In a further embodiment, the above-mentioned core comprises from 4 to 7 amino acids. In a further embodiment, the above-mentioned core comprises from 4 to 6 amino acids. In a further embodiment, the above-mentioned core comprises 4, 5 or 6 amino acids.

In an embodiment, the above-mentioned heteropeptide comprises from 4 to 10 amino acids. In an embodiment, the above-mentioned heteropeptide comprises from 4 to 9 amino acids. In an embodiment, the above-mentioned heteropeptide comprises from 4 to 8 amino acids. In a further embodiment, the above-mentioned heteropeptide comprises from 4 to 7 amino acids. In a further embodiment, the above-mentioned heteropeptide comprises from 4 to 6 amino acids. In a further embodiment, the above-mentioned heteropeptide comprises 4, 5 or 6 amino acids.

In another aspect, the present invention provides a heteropeptide suitable for forming a low fouling self-assembled monolayer (SAM) consisting of the core defined above.

In another aspect, the present invention provides a heteropeptide suitable for forming a low fouling self-assembled monolayer (SAM) of the following formula IV:

$$R^1\text{—}X^1\text{—}R^2 \tag{IV}$$

wherein $X^1$ is the core defined above; $R^1$ is a binding moiety or is absent; and $R^2$ is a binding moiety or is absent. In an embodiment, $R^1$ and/or $R^2$ are non-peptidic moieties.

The heteropeptide of the invention may be produced by expression in a host cell comprising a nucleic acid encoding the heteropeptide (recombinant expression) or by chemical synthesis (e.g., solid-phase peptide synthesis). Peptides can be readily synthesized by automated solid phase procedures well known in the art. Suitable syntheses can be performed by utilizing "T-boc" or "Fmoc" procedures. Techniques and procedures for solid phase synthesis are described in for example *Solid Phase Peptide Synthesis: A Practical Approach*, by E. Atherton and R. C. Sheppard, published by IRL, Oxford University Press, 1989. Alternatively, the peptides may be prepared by way of segment condensation, as described, for example, in Liu et al., *Tetrahedron Lett.* 37: 933-936, 1996; Baca et al., *J. Am. Chem. Soc.* 117: 1881-1887, 1995; Tam et al., *Int. J. Peptide Protein Res.* 45: 209-216, 1995; Schnolzer and Kent, *Science* 256: 221-225, 1992; Liu and Tam, *J. Am. Chem. Soc.* 116: 4149-4153, 1994; Liu and Tam, *Proc. Natl. Acad. Sci. USA* 91: 6584-6588, 1994; and Yamashiro and Li, *Int. J. Peptide Protein Res.* 31: 322-334, 1988). Other methods useful for synthesizing the peptides are described in Nakagawa et al., *J. Am. Chem. Soc.* 107: 7087-7092, 1985.

Commercial providers of peptide synthetic services may also be used to prepare synthetic peptides in the D- or L-configuration. Such providers include, for example, ADVANCED CHEMTECH® (Louisville, Ky.), APPLIED BIOSYSTEMS® (Foster City, Calif.), ANASPEC® (San Jose, Calif.), and CELL ESSENTIALS® (Boston, Mass.).

The heteropeptides of the invention can be purified by many techniques well known in the art, such as reverse phase chromatography, high performance liquid chromatography (HPLC), ion exchange chromatography, size exclusion chromatography, affinity chromatography, gel electrophoresis, and the like. The actual conditions used to purify a particular peptide or peptide analog will depend, in part, on synthesis strategy and on factors such as net charge, hydrophobicity, hydrophilicity, and the like, and will be apparent to those of ordinary skill in the art. For affinity chromatography purification, any antibody which specifically binds the peptide or peptide analog may for example be used.

In embodiments, the N- and/or C-terminal amino acids may be modified by amidation, acetylation, acylation or other modifications known in the art.

In an embodiment, the N- and/or C-terminal of the above-mentioned heteropeptide is used for direct immobilization/attachment (covalent or non-covalent) to the solid support. In an embodiment, attachment to the solid support is via the N-terminal end of the peptide, thus leaving the carboxyl terminus free for various chemistries (e.g., EDC/NHS chemistry) to immobilize molecules (e.g., a biomolecule, such as a polypeptide of interest). Direct attachment via the N-terminal end of the peptide may be achieved, for example, by conventional EDC/NHS chemistry using a solid support comprising free carboxyl groups (e.g., a carboxy-functionalized solid support, as described below).

In an embodiment, at least one end (e.g., the N- and/or C-terminal end) of the above-mentioned heteropeptide is used for immobilization/attachment (covalent or non-covalent) to the solid support indirectly, via a peptide immobilization moiety/linker (binding moiety $R^1$ or $R^2$ in formula IV above). Therefore, in an embodiment, the above-mentioned heteropeptide is in the form "peptide immobilization moiety—core" or "core—peptide immobilization moiety".

In an embodiment, at least one end (e.g., the N- and/or C-terminal end) of the above-mentioned heteropeptide is used for immobilization/attachment (covalent or non-covalent) to a target molecule (e.g., a biomolecule such as a polypeptide) indirectly, via a molecule attachment moiety/linker (binding moiety $R^1$ or $R^2$ in formula IV above). Therefore, in an embodiment, the above-mentioned heteropeptide is in the form "molecule attachment moiety—core" or "core—molecule attachment moiety".

In another embodiment, one end (e.g., the N- and/or C-terminal end) of the above-mentioned heteropeptide is used for immobilization/attachment (covalent or non-covalent) to the solid support indirectly, via a first moiety (peptide immobilization moiety), and the other end is used for attachment (covalent or non-covalent) to a target molecule (e.g., a biomolecule such as a polypeptide) indirectly, via a second moiety (molecule attachment moiety). Therefore, in an embodiment, the above-mentioned heteropeptide is in the form:

"peptide immobilization moiety—core—molecule attachment moiety" or

"molecule attachment moiety—core—peptide immobilization moiety".

The above-mentioned noted peptide immobilization moiety and molecule attachment moiety may be identical or different.

It should thus be understood that in formula IV defined above, binding moieties $R^1$ and/or $R^2$, if present, may either represent the peptide immobilization moiety or the molecule attachment moiety, depending on the end of the peptide attached or intended to be attached to the solid support. In the situation where the peptide is attached or intended to be attached to the solid support through its N-terminal end via a moiety, $R^1$ represents the peptide immobilization moiety. Alternatively, in the situation where the peptide is attached or intended to be attached to the solid support through its C-terminal end via a moiety, $R^2$ represents the peptide immobilization moiety.

The peptide immobilization moiety and/or molecule attachment moiety ($R^1$ and/or $R^2$) may be any suitable affinity tag, ligand or reactive moiety permitting the non-covalent or covalent attachment of the heteropeptide to a corresponding affinity tag, ligand or reactive moiety present on the solid support and/or on the target molecule.

A variety of moiety/linker or crosslinking agents are known for interconnection of a variety of reactive groups. In an embodiment, the peptide immobilization moiety and/or molecule attachment moiety ($R^1$ and/or $R^2$) is an affinity tag/moiety capable of binding to a corresponding ligand/moiety present on the surface on the solid support and/or in the target molecule. In an embodiment, the peptide immobilization moiety and/or molecule attachment moiety is a component of typical affinity tags-based systems, such as NTA—"His-Tag" systems, biotin—avidin/streptavidin systems, glutathione S-transferase (GST)—glutathione systems, Maltose Binding Protein (MBP)—amylose systems, DNA—DNA hybridization systems, RNA—RNA hybridization systems, protein—nucleic acid systems, as well as antigen—antibody systems (the other component of the system being present on the solid support and/or the target molecule).

Figure 7:
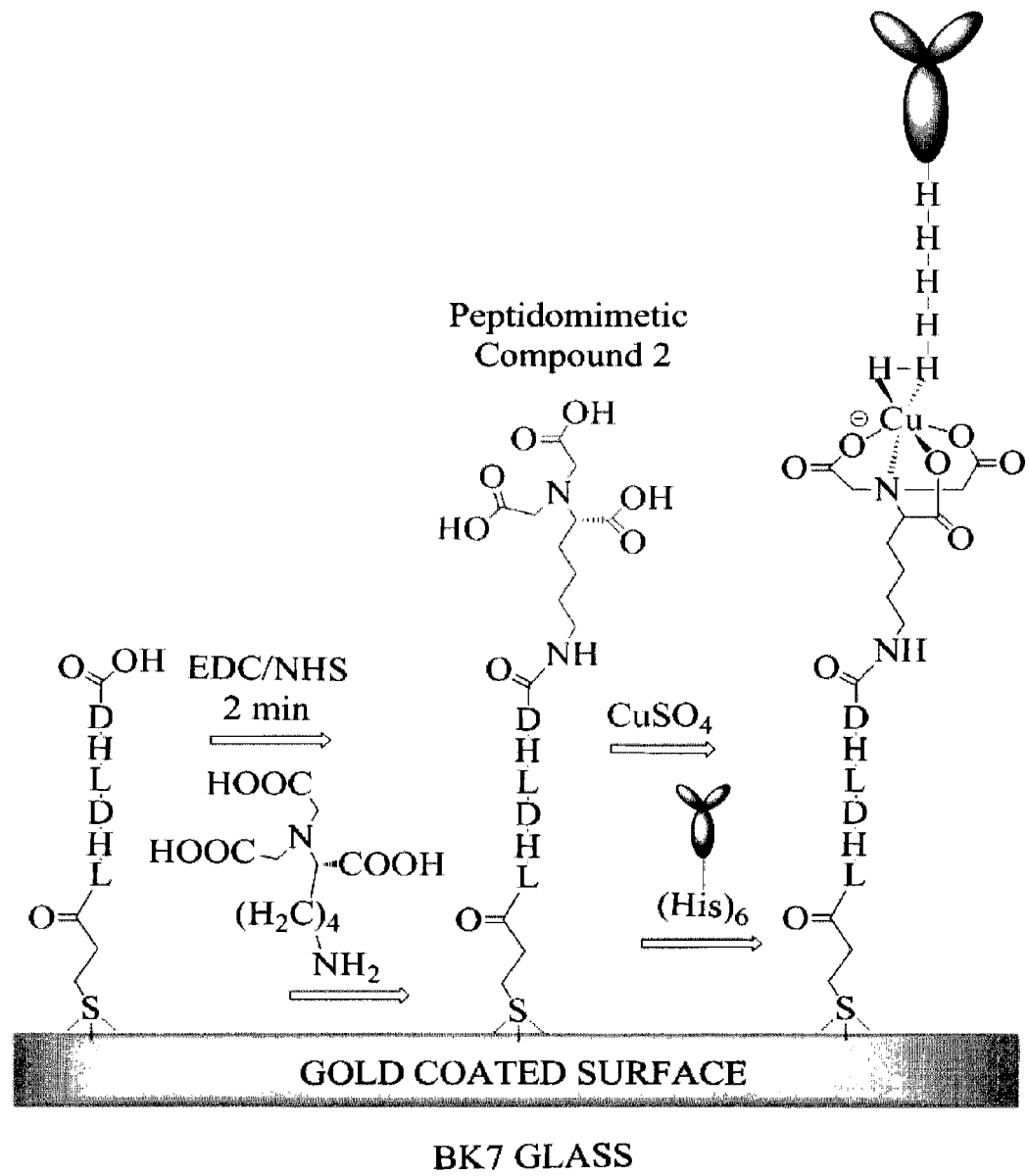
FIG. 7 shows a schematic representation of the peptidomimetic monolayer binding His-tagged biomolecules. An antibody is shown in the schematic, but the surface is not limited to the binding of His-tagged antibodies.

In an embodiment, the peptide immobilization moiety and/or molecule attachment moiety ($R^1$ and/or $R^2$) may be generated by modifying the N- and/or C-terminal end(s) of peptide, i.e. by incorporating a moiety using conventional chemistry. For example, the N- and/or C-terminal end(s) of the heteropeptides may be modified to include a moiety capable of binding His-tagged proteins, notably a nitriloacetic acid-(NTA-) based moiety such as the aminobutanylated derivative of NTA called Nα,Nα-bis(carboxymethyl)-L-lysine. Such NTA-based moiety may be covalently linked (through an amide bond) to the C-terminal end of the heteropeptides using conventional EDC/NHS chemistry (see FIG. 7). Therefore, in an embodiment, the above-mentioned peptide immobilization moiety and/or molecule attachment moiety ($R^1$ and/or $R^2$) is a NTA-based moiety. In a further embodiment, the above-mentioned molecule attachment moiety is a NTA-based moiety linked to the C-terminal end of the heteropeptide ($R^2$).

In an embodiment, the peptide immobilization moiety is a gold reactive moiety (i.e. a moiety capable of covalent or non-covalent binding to gold). In an embodiment, the peptide immobilization moiety comprises a thiol moiety (e.g., alkanethiols), which is useful for covalently binding the peptide to a solid support coated with gold via the well known thiol chemistry. Incorporation of a thiol moiety to the N-terminal end of a peptide may be performed, for example, using Fmoc protected amino acids coupled to a phenoxy resin, followed by reaction with a carboxylic acid thiol (mercapto acid) such as a $C_3$- to $C_{16}$-carboxylic acid thiol. In an embodiment, the above-mentioned carboxylic acid thiol is a 3-mercaptopropionic acid (3-MPA).

In an embodiment, the above-mentioned peptide immobilization moiety is a compound of formula V:

$$HS-(CH_2)_n-COOH \quad (V)$$

wherein n=1 to 20.

In another embodiment, the above-mentioned peptide immobilization moiety is a compound of formula VI:

$$HS-(CH_2)_m-CHR-(CH_2)_p-COOH \quad (VI)$$

wherein
R is any chemical group such as $NH_2$, OH, SH, COOH, non restrictively,
m is greater than or equal to 0 and less than or equal to 20,
p is greater than or equal to 0 and less than or equal to 20, and m+p is less than or equal to 20.

In another embodiment, the above-mentioned peptide immobilization moiety is a compound of formula IV:

$$HS-(R)-COOH \quad (VII)$$

wherein R is any organic chemical group, combination of organic and inorganic compounds, capable of forming a monolayer on a surface.

In an embodiment, the peptide immobilization moiety is a diazonium salt moiety permitting electrochemical immobilization on a metal surface. In another embodiment, the peptide immobilization moiety is a silane moiety permitting immobilization on glass surface.

In an embodiment, the above-mentioned peptide immobilization moiety ($R^1$) is attached to the N-terminal end of the heteropeptide.

In an embodiment, the above-mentioned molecule attachment moiety ($R^2$) is attached to the C-terminal end of the heteropeptide.

In an embodiment, the above-mentioned core ($X^1$) is: SSSDD (SEQ ID NO:10), HHHDD (SEQ ID NO:11), LLLDD (SEQ ID NO:12), LLLSS (SEQ ID NO:13), LLLHH (SEQ ID NO:14), HHHSS (SEQ ID NO:15), DDDHH (SEQ ID NO:16), DDDSS (SEQ ID NO:17), SSSHH (SEQ ID NO:18), LHDLHD (SEQ ID NO: 35), SHDSHD (SEQ ID NO: 34) or DSDSD (SEQ ID NO:32).

In an embodiment, the above-mentioned heteropeptide is: SSSDD (SEQ ID NO:10), HHHDD (SEQ ID NO:11), LLLDD (SEQ ID NO:12), LLLSS (SEQ ID NO:13), LLLHH (SEQ ID NO:14), HHHSS (SEQ ID NO:15), DDDHH (SEQ ID NO:16), DDDSS (SEQ ID NO:17), SSSHH (SEQ ID NO:18), LHDLHD (SEQ ID NO: 35), SHDSHD (SEQ ID NO: 34) or DSDSD (SEQ ID NO:32) (i.e., $R^1$ and $R^2$ are absent).

In an embodiment, the above-mentioned heteropeptide is: 3-MPA-SSSDD (SEQ ID NO:19), 3-MPA-HHHDD (SEQ ID NO:1), 3-MPA-LLLDD (SEQ ID NO:20), 3-MPA-LLLSS (SEQ ID NO:21), 3-MPA-LLLHH (SEQ ID NO:22), 3-MPA-HHHSS SEQ ID NO:23), 3-MPA-DDDHH (SEQ ID NO:24), 3-MPA-DDDSS (SEQ ID NO:25), 3-MPA-SSSHH (SEQ ID NO:26), 3-MPA-LHDLHD (SEQ ID NO:29), 3-MPA-SHDSHD (SEQ ID NO:33) or 3-MPA-DSDSD (SEQ ID NO:32) (i.e. $R^1$ is a 3-MPA moiety and $R^2$ is absent).

In an embodiment, the above-mentioned heteropeptide is: SSSDD-NTA (SEQ ID NO:36), HHHDD-NTA (SEQ ID NO:37), LLLDD-NTA (SEQ ID NO:38), LLLSS-NTA (SEQ ID NO:39), LLLHH-NTA (SEQ ID NO:40), HHHSS-NTA (SEQ ID NO:41), DDDHH-NTA (SEQ ID NO:42), DDDSS-NTA (SEQ ID NO:43), SSSHH-NTA (SEQ ID NO:44), LHDLHD-NTA (SEQ ID NO:45), SHDSHD-NTA (SEQ ID NO:46) or DSDSD-NTA (SEQ ID NO:47) (i.e. $R^1$ is absent and $R^2$ is a nitriloacetic acid-(NTA) based moiety).

In an embodiment, the above-mentioned heteropeptide is: 3-MPA-SSSDD-NTA (SEQ ID NO:48), 3-MPA-HHHDD-NTA (SEQ ID NO:49), 3-MPA-LLLDD-NTA (SEQ ID NO:50), 3-MPA-LLLSS-NTA (SEQ ID NO:51), 3-MPA-LLLHH-NTA (SEQ ID NO:52), 3-MPA-HHHSS-NTA (SEQ ID NO:53), 3-MPA-DDDHH-NTA (SEQ ID NO:54), 3-MPA-DDDSS-NTA (SEQ ID NO:55), 3-MPA-SSSHH-NTA (SEQ ID NO:56), 3-MPA-LHDLHD-NTA (SEQ ID NO:57), 3-MPA-SHDSHD-NTA (SEQ ID NO:58) or 3-MPA-DSDSD-NTA (SEQ ID NO:59) ($R^1$ is a 3-MPA moiety and $R^2$ is a nitriloacetic acid-(NTA) based moiety).

The above-mentioned solid support may be any solid support which permits the binding (e.g., immobilization) of the peptide defined above and which may be used for the desired application (e.g., in biosensing applications). It includes for example glass or plastic plates/slides. In an embodiment, the above-mentioned solid support is a glass solid support. In embodiments, the above-mentioned plates/slides may be modified (e.g., coated, chemically modified, derivatized) prior to immobilization of the peptide. In an embodiment, the solid support is modified to permit or facilitate the covalent or non-covalent immobilization of peptides, using any method known in the art. An example of such modification is the functionalization/carboxylation of a solid support (glass surface), as described in Example 13 below. The solid support may be either amino- or carboxy-functionalized, depending on whether immobilization of the peptides through their C- or N-terminal ends is desired. The carboxylation of the solid support surface permit to immobilize the peptides through their N-terminal, for example using N-dimethylaminopropyl-N'-ethylcarbodiimide hydrochloride (EDC)/N-hydroxysuccinimide (NHS) chemistry. In an embodiment, the carboxylation of the glass surface comprises: attaching a trimethoxysilane-$(CH_2)_n$-$NH_2$ moiety to said glass surface, wherein n=1 to 20, in embodiments 1 to 10, 1 to 6, or 3 (3-aminopropyl)trimethoxysilane); and attaching (via EDC/NHS chemistry, for example) a carboxylic acid (polycarboxylic acids such as citric acid) to said trimethoxysilane-$(CH_2)_n$-$NH_2$ moiety, for example using a carboxylic acid salt (e.g., potassium citrate). Such carboxy-functionalized glass surfaces (exposing free carboxylic groups of the polycarboxylic acid) permit the immobilization of peptides through their N-terminal via EDC/NHS chemistry.

In another embodiment, the solid support is coated with gold, which permits the immobilization of peptides comprising, for example, a thiol moiety (e.g., 3-mercaptopropionic acid (3-MPA)), as described in more detail below. The solid support may be modified/coated using any conventional moiety capable of binding to a corresponding moiety (peptide immobilization linker) of the peptides to be immobilized, e.g., using typical affinity tags-based systems such as NTA—"His-Tag" systems, biotin—avidin/streptavidin systems, glutathione S-transferase (GST)—glutathione systems, Maltose Binding Protein (MBP)—amylose systems, DNA—DNA hybridization systems, RNA—RNA hybridization systems, protein—nucleic acid systems, as well as antigen—antibody systems.

As used herein, the term "biosensor" refers to any system or device which is used to detect, quantify, or determine the activity of analytes such as biomolecules (e.g., nucleic acids, polypeptides, carbohydrates, lipids, steroids or the like). Such a biosensor system or device generally comprises means for detecting a signal. Therefore, the low fouling substrate described above may be used in any biosensor device or system. In an embodiment, the above-mentioned biosensor is an electrochemical biosensor (see, for example, Porfirieva, A. et al., *Electroanalysis* 2007, 19: 1915), a surface acoustic wave biosensor (see, for example, Sankaranarayanan, S. K. R. S. et al., *Physical Review E (Statistical, Nonlinear, and Soft Matter Physics)* 2008, 77: 066308) or a surface plasmon resonance (SPR) biosensor (see, for example, Furuya, M. et al., *Biorg. Med. Chem.* 2006, 14: 537 and Masson, J. F. et al., *Anal. Bioanal. Chem.* 2006, 386: 1951). In a further embodiment, the above-mentioned biosensor is a SPR biosensor.

In another aspect, the present invention provides a method for reducing nonspecific adsorption on a solid support (e.g., a biosensor solid support) or for preparing the above-mentioned low fouling substrate, comprising contacting said solid support with the peptide defined above under conditions permitting binding (e.g., covalent binding) of said peptide to said solid support.

In another aspect, the present invention provides a kit for reducing the nonspecific adsorption on a solid support, said kit comprising the heteropeptide defined above. In an embodiment, the above-mentioned kit further comprises instructions for coating a solid support with said heteropeptide. In an embodiment, the above-mentioned kit further comprises a solid support. The kit may further comprise one or more reagents for coating said solid support with said heteropeptide, as well as suitable containers, buffers, washing solutions, etc.

In another aspect, the present invention provides a method for preparing the above-mentioned biosensor chip comprising contacting a biosensor solid support with the peptide defined above under conditions permitting binding (e.g., covalent binding) of said peptide to said solid support.

In an embodiment, the above-mentioned solid support is coated with a metal such as gold or silver. In another embodiment, the above-mentioned solid support is chemically-modified (functionalized). In a further embodiment, the above-mentioned solid support is a SPR solid support. In an embodiment, the above-mentioned heteropeptide forms a monolayer on the surface of said solid support.

In an embodiment, the nonspecific surface coverage due to nonspecific adsorption ($\Gamma_{nonspecific}$) of the above-mentioned low fouling substrate, as measured by SPR using undiluted bovine serum on a gold-coated solid support, is about 200 ng of protein/cm$^2$ or less, in a further embodiment about 150 ng of protein/cm$^2$ or less, in a further embodiment about 100 ng of protein/cm$^2$ or less, in a further embodiment about 90 ng of protein/cm$^2$ or less, in a further embodiment about 80 ng of protein/cm$^2$ or less, in a further embodiment about 70 ng of protein/cm$^2$ or less, in a further embodiment about 60 ng of protein/cm$^2$ or less, in a further embodiment about 50 ng of protein/cm$^2$ or less, in a further embodiment about 40 ng of protein/cm$^2$ or less, in a further embodiment about 30 ng of protein/cm$^2$ or less, in a further embodiment about 20 ng of protein/cm$^2$ or less.

The low fouling substrate of the invention exhibits lower levels of non-specific adsorption, and therefore may be used in a variety of applications where decreased non-specific adsorption is desired. For example, it is desirable to have lower levels of non-specific binding in biosensing, biodetection, diagnostic applications, as well as for binding studies. With lower non-specific binding, the signal to noise ratio is optimized, and further, it is possible to detect biological components of interest which are present at lower concentrations, and also possible to detect such components in more complex mixtures.

The low fouling substrate of the invention may be used to detect the binding between a first molecule (nucleic acid, polypeptide, etc.), attached to the substrate, and a second molecule present in a sample (small molecule, polypeptide, nucleic acid). The first molecule (e.g., a polypeptide) may be attached to the heteropeptides present on the solid support using conventional chemistry suitable for peptide coupling (e.g., EDC/NHS chemistry). Alternatively, the heteropeptides present on the solid support may be modified to comprises a moiety (molecule attachment linker) capable of binding a moiety present on the first molecule. Such a strategy is particularly suitable for molecules whose structure and/or activity is altered when using conventional chemistry (e.g., EDC/NHS chemistry) for attachment. For example and as described above, the carboxy-terminal end of the heteropeptides attached to the solid support may be modified to include a moiety capable of binding His-tagged molecules, notably a nitriloacetic acid-(NTA) based moiety such as the aminobutanylated derivative of NTA called Nα,Nα-bis(carboxymethyl)-L-lysine. Such NTA-based moiety may be covalently linked to the C-terminal end of the heteropeptides using conventional EDC/NHS chemistry. In the presence of metal ions such as $Ni^{2+}$, $Ca^{2+}$, $Cu^{2\alpha}$ or $Fe^{3+}$, such moiety binds to a His-tagged molecule, such as a His-tagged polypeptide. The NTA-modified low fouling substrate may be regenerated by washing/rinsing with an imidazole solution (to release the His-tagged molecule). In an embodiment, the NTA-modified low fouling substrate is regenerated with concentrated histidine, imidazole or ethylene diaminetetraacetic acid (EDTA) solutions, or by varying the pH.

Any other affinity tag-based systems may be used to attach a target molecule to the heteropeptides present on the above-mentioned low fouling substrate.

The above-mentioned low fouling substrate may be modified to further comprise a suitable capture reagent (molecule) attached/bound thereto, to enable binding/detection of an analyte of interest in a sample. "Capture reagent" as used herein refers to any molecule or ligand which is capable of interacting or binding with a binding partner or ligand. For example, in biological applications, the antibody-antigen interaction is often exploited, in which case either an antibody (or an antigen-binding fragment thereof) or its antigen (e.g., a polypeptide) may be used as the capture reagent. Another example of an interaction which may be used is a biological receptor-ligand interaction. It should be understood that the low fouling substrate described above may be used to detect any molecule-molecule interaction (e.g., biomolecule-biomolecule interaction) such as any protein-protein interaction, nucleic acid-protein interaction, nucleic acid-nucleic acid interaction, cofactor-protein interaction, protein-drug interaction.

The low fouling substrate may be used in diagnostic applications, for example to detect the presence and/or level of an analyte of interest (e.g. a marker for a certain disease/condition) in a biological sample (e.g., blood, serum, plasma, urine, saliva). A capture reagent capable of binding to the analyte of interest (e.g., an antibody specific for the marker) is immobilized on the low fouling substrate, the biological sample is put in contact with the immobilized capture reagent, and the absence or presence of binding, and/or the level thereof, is determined. The absence or presence of binding, and/or the level thereof, is indicative of the absence, presence and/or level of the analyte of interest in the sample, which in turn may be used to diagnose a disease/condition.

The low fouling substrate may be used in drug screening applications, i.e., to screen for compounds capable of interacting or binding to a target biomolecule immobilized on its surface. Accordingly, the present invention also provides a method for determining whether a test agent binds to a molecule, said method comprising: (i) providing the substrate defined above comprising the molecule immobilized thereon; (ii) contacting said test agent with said immobilized molecule; (iii) determining whether said test agent binds to said molecule. The present invention also provides a method for determining whether a binding partner or ligand for a molecule is present in a test sample, said method comprising: (i) providing the substrate defined above comprising the molecule immobilized thereon; (ii) contacting said test sample with said immobilized molecule; (iii) determining whether binding to said immobilized molecule has occurred; wherein said binding is indicative that a binding partner or ligand for said molecule is present in said test sample. The present invention also provides a method for determining whether a test agent binds to a molecule, said method comprising: (i) immobilizing said molecule on the above-mentioned substrate; (ii) contacting said test agent with said immobilized molecule; and (iii) determining whether said test agent binds to said molecule. The present invention also provides a method for determining whether a binding partner or ligand for a molecule is present in a test sample, said method comprising: (i) immobilizing said molecule on the above-mentioned substrate; (ii) contacting said test sample with said immobilized molecule; (iii) determining whether binding to said immobilized molecule has occurred; wherein said binding is indicative that a binding partner or ligand for said molecule is present in said test sample, and the absence of binding is indicative that a binding partner or ligand for said molecule is not present in said test sample.

The above-mentioned methods may further comprises one or more washing/rinsing steps to minimize the non-specific binding. The above-mentioned methods may also comprises one or more elution steps, which may be useful for example to collect the binding partner or ligand (for identification and/or further characterization), or to regenerate the substrate (with or without the immobilized molecule), which may then be re-utilized.

The determination of the binding may be performed using any suitable device or systems, for example the biosensing devices/systems described above.

The above-noted screening method or assay may be applied to a single test compound or to a plurality or "library" of such compounds (e.g., a combinatorial library). Any such compounds may be utilized as lead compounds and further modified to improve their therapeutic, prophylactic and/or pharmacological properties for preventing and/or treating the target disease or condition.

Test compounds (e.g., drug candidates) may be obtained from any number of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means.

Screening assay systems may comprise a variety of means to enable and optimize useful assay conditions. Such means may include but are not limited to: suitable buffer solutions, for example, for the control of pH and ionic strength and to provide any necessary components for optimal activity and stability (e.g., protease inhibitors), temperature control means for optimal activity and/or stability and detection means to enable the detection of the activity of the molecule. In an embodiment, the detection is performed by measuring the surface plasmon resonance (SPR) signal, using a suitable SPR system/device. In an embodiment, the above-mentioned biomolecule is a polypeptide. Polypeptide as used herein refers to a molecule composed of monomers (amino acids) linearly linked by amide bonds (also known as peptide bonds). It indicates a molecular chain of amino acids and does not refer to a specific length of the product. Thus, peptides, dipeptides, tripeptides, oligopeptides as well as full-length proteins (enzymes, receptors, transcription factors, etc.), fragments thereof (e.g., comprising a domain of interest such as an active site and/or a ligand-binding domain), variants thereof (e.g., a mutated form of a native protein or fragment thereof) are included within the definition of polypeptide. Post-translational modifications of the polypeptide, for example, glycosylations, acetylations, phosphorylations, and the like are also encompassed.

The present invention further provides a system comprising the above-mentioned low fouling substrate and capture reagent and a suitable detection means (to convert the detected binding to a suitable binding signal). The system may comprise further components, such as suitable means to introduce the sample to the system, and an incubation chamber to allow the sample to be put into contact with the low fouling substrate. In an embodiment, the above-mentioned system is a SPR-based system.

The present invention further provides a use of the above-mentioned low fouling substrate and capture reagent, for detecting or sensing an analyte in a sample. The present invention further provides a method of detecting or sensing an analyte in a sample, comprising contacting the sample with the above-mentioned low fouling substrate comprising the capture reagent.

As a further example, non-specific adsorption is a major cause for prosthesis and implant rejection (Morimoto, N. et al. *Biomaterials* 2002, 23: 4881). Accordingly, in another aspect, the present invention provides an implant or prosthesis or a portion thereof, comprising the heteropeptide defined above attached thereto. The present invention further provides a use of the just noted prosthesis or implant comprising the heteropeptide defined above attached thereto, for reducing prosthesis or implant rejection. The present invention further provides a use of the above-mentioned low fouling substrate for the manufacture of a prosthesis or implant for reducing prosthesis or implant rejection. The present invention further provides a method of reducing prosthesis or implant rejection, comprising attaching or implanting to a prosthesis or implant recipient the prosthesis or implant comprising the heteropeptide defined above attached thereto.

MODE(S) FOR CARRYING OUT THE INVENTION

The present invention is illustrated in further details by the following non-limiting examples.

Example 1

Materials and Methods

Materials.

Microscope slides (BK7, 22 mm×22 mm), anhydrous methanol and imidazole were bought from Fisher Scientific. Sterile filtered adult bovine serum, L-histidine, N-ethyl-N'-(3-dimethylaminopropyl)-carbodiimide (EDC), N-hydroxysuccinimide (NHS), ethylene diaminetetraacetic acid (EDTA) and Nα,Nα-bis(carboxymethyl)-L-lysine hydrate were purchased from SIGMA-ALDRICH®. Gold (purity of 99.99%) and chromium were acquired from ESPI Metals. Dimethylformamide (DMF, ACS grade) was bought from EMD chemicals. Phosphate buffered saline 1×(PBS), pH=7.4 was prepared by CELLGRO® from Mediatech.

Synthesis of 3-MPA-heteropeptide-OH.

Amino acids were bought from NOVABIOCHEM® (distributed by EMD biochemicals, Ville Mont-Royal, QC) with the amine and side chain protected (Fmoc-Leu-OH, Fmoc-His(Trt)-OH, Fmoc-Asp(OtBu)-OH, Fmoc-Ser(tBu)-OH) to avoid multiple couplings and side reactions during the solid phase synthesis. Polystyrene based resin (100-200 mesh, NOVABIOCHEM®, Ville Mont-Royal, QC) exposing a hydroxymethylphenoxy linker was first immersed in dichloromethane (DCM) twice for 30 minutes to prepare the linker for the coupling of a first amino acid to the phenoxy groups. All reactions took place in an SPE tube equipped with a cellulose filter to minimize loss of resin and to facilitate rinsing of the resin. A solution containing 6 equivalents of the amino acid to attach to the resin mixed with 3 equivalents of diisopropylcarbodiimide (SIGMA-ALDRICH®, Milwaukee, Wis.) was prepared in N,N-dimethylformamide (DMF) for immersion of the resin. Thereafter, a DMF solution containing a catalytic amount of 4-(dimethylamino)pyridine (DMAP, FLUKA®, Milwaukee, Wis.) was quickly mixed with the previous solution. The reaction mixture was stirred overnight, at room temperature. The resin was then rinsed three times with DMF, three times with methanol and three times with DCM, 3 minutes for each rinsing step. This rinsing method was also used after each of the following steps. A small amount of the resin is used determine coupling efficiency. A first portion of the resin was used to perform a Kaiser test in order to verify that the coupling was complete. A second portion was immersed in a 20:80 piperidine (SIGMA-ALDRICH®, Milwaukee, Wis.) and DMF solution for 30 minutes to remove the N-terminal Fmoc protecting group, for peptide growth. The Kaiser test was repeated with the deprotected portion to verify the completion of the deprotection reaction. The subsequent coupling reactions were performed with 3 equivalents of the amino acid, 3 equivalents of 2-(1H-Benzotriazole-1-yl)-1,1,3,3-tetramethyluronium (HBTU, NOVABIOCHEM®) and 9 equivalents of N-ethyl-diisopropylamine (DIEA) in DMF for two hours. The final coupling was accomplished with one equivalent of N-3-mercaptopropionic acid (3-MPA, SIGMA-ALDRICH®) instead of 3 equivalents of amino acid. Thereafter, a one hour reaction in a solution of 95% trifluoroacetic acid (TFA, EMD biochemicals), 2.5% triethylsilane (TES, Alfa Aesar, Ward Hill, Mass.) and 2.5% water cleaved the peptide from resin to yield the 3-MPA-$(AA)_n$-OH, with n corresponding to the number of amino acids in the peptide and AA corresponding to the amino acid sequence synthesized. TFA was evaporated and the peptide was precipitated in diethyl ether to recover the pure 3-MPA-$(AA)_n$-OH. The composition of each peptide was verified using LC-ESI-MS. The yield varied between 15% and 65% depending on the structure of the peptide.

Preparation of Peptidic Monolayers on the Au Surface of the SPR Sensor.

Microscope slides (BK7, 22×22 mm) were coated with a 3 nm titanium (Ti) adhesion layer and a 50 nm gold (Au) layer (purity 99.99%, ESPI metals) using a Cressington™ 308R sputter coater. These Au-coated SPR slides were immersed for at least 16 h in a 5 mM peptide solution in absolute ethanol to form a well-ordered monolayer (Masson, J. F. et al. *Talanta* 2004, 64: 716). Four replicates were prepared for each 3-MPA-peptide. The SAM formed on the SPR sensors was extensively rinsed with DMF and ethanol and dried. The mid-IR spectrum of the peptide monolayers immobilized on the SPR sensors was measured in attenuated total reflectance (ATR). Mid-IR spectra were recorded using a BRUKER TENSOR® 27 equipped with a Ge-ATR module.

SPR Instrumentation.

The SPR instrument is according to Bolduc et al. (Bolduc et al, *Talanta*, 2009, 77(5):1680-7. Epub 2008 Oct. 17). In brief, the SPR sensor is comprised of a halogen or LED light source, fiber optics to deliver the light from the light source to a collimator. The collimator launches the light parallel to the long face of a dove prism, which reflects the light at 72.8°. The exiting light is still parallel to the prism and collected using a lens. The light is delivered from the fiber optic to the spectrophotometer, and data is sent for analysis with software. The SPR sensor as described above, is placed into contact with the dove prism using index matching fluid and a flow cell delivers the solution to the sensor.

SPR and Contact Angle Measurements.

The surface coverage for each monolayer was measured according to the change in response of the SPR sensor in PBS for the bare Au surface relative to the peptide-coated Au surface. To measure the formation of the monolayers, each SPR sensor was mounted on a custom-made SPR instrument in the Kretschmann configuration based on a dove prism with wavelength interrogation as previously described (Bolduc et al., 2009, supra). An Ocean Optics™ USB4000 fibre optic spectrometer ranging from 550 to 850 nm was used to acquire the spectral information processed with Matlab to obtain the SPR sensorgram. A 25 μL Teflon fluidic cell positioned on top of the SPR sensors was used to inject the solutions required to functionalize with the recognition element and detect the analytes of interest. The SPR response was acquired at a frequency of 1 Hz. The s-polarized reference was acquired in PBS buffer before monitoring a 5 minute baseline in p-polarization. PBS was replaced with crude bovine serum (76 mg/mL protein) for 20 minutes and rinsed with PBS for 5 minutes to quantify the amount of non-specifically adsorbed proteins.

Immobilization of Anti-IgG or Anti-MMP3 and Detection of the Specific Analytes.

Based on the results obtained in limiting nonspecific protein adsorption experiments, 3-MPA-HHHDD-OH was selected to construct SPR biosensors, as described below. The SAM was formed as described above, the SPR sensor is placed on the SPR spectrometer equipped with a fluidic cell for at least 5 minutes of stabilization in Millipore™-filtered water. Each solution needed to the construction of a SPR affinity biosensor was injected to react the surface with chemicals procuring the specificity to the SPR sensor, before the injection of the solution containing the analyte. The measurement starts with 2 minutes of reference in Millipore™-filtered water. Then an aqueous solution composed of 25 mM N-ethyl-N'-(3-dimethylaminopropyl)-carbodiimide (EDC, FLUKA®) and 5 mM of N-hydroxysuccinimide (NHS, SIGMA-ALDRICH®) was injected for 2 minutes followed by a rinsing with PBS adjusted at a pH of 4.5 water for 2 more minutes. A solution prepared with 25 μg/mL of the antibody (anti-human IgG or anti-human MMP-3 according to the experiments described below) in regular PBS (pH 7.4) then replaced the preceding solution for 15 minutes. The excess of antibody was rinsed with PBS for 2 minutes before a 5-minute exposition to a 1M ethanolamine solution adjusted to pH 8.5. The SPR sensor was rinsed once more for 5 minutes in PBS before injection of the analyte of interest. The detection assay was performed for 10 minutes with a saline solution of IgG or MMP-3 (depending on the antibody immobilized) and was followed by a 5-minute measurement in PBS.

Detection and Quantification of MMP-3 in Complex Matrices.

3-MPA-HHHDD-OH SAM-based biosensors were used to investigate the potential of such devices as direct detection tools in blood serum and diluted blood serum. Biosensors were prepared as described above. In this experiment, a two-minute exposition to bulk bovine serum preceded a spiked bovine serum solution to verify that no nonspecific interaction occurred on these biosensors.

Synthesis of the Peptidomimetic Monolayer Binding His-Tagged Biomolecules.

The synthesis of the peptidomimetic monolayer binding His-tagged biomolecules was performed directly on the SPR sensors (FIG. 7), based on the optimal peptide 3-MPA-LH-DLHD-OH (see results below, and Table II). The following solutions are aqueous and the SPR sensors were rinsed in ultrapure water following each step. The peptide monolayer immobilized on the SPR sensor was reacted with a solution composed of 100 mM EDC and 20 mM NHS for 2 minutes, followed by a 1 hour reaction with 40 mM Nα,Nα-bis(carboxymethyl)-L-lysine hydrate. The final step was a 10 minute exposition to 100 mM $CuSO_4$, during which $Cu^{2+}$ binds to the peptidomimetic monolayer. The SPR sensors were rinsed in ultrapure water and dried using a moderate flow of nitrogen. The product of each reaction was monitored using FTIR. In this configuration, the peptide monolayer chelates copper and copper chelates His-tagged biomolecules. Thus, the surfaces were analyzed using x-ray photoelectron spectroscopy (XPS) to ensure the presence of $Cu^{2+}$ on the SPR sensors modified with the peptidomimetic monolayer binding His-tagged biomolecules. A VG ESCALAB™3 MKII equipped with a Mg Kα source running at 300 W scanning from 50 to 100 Å deep provided the XPS spectral information.

His-Tagged Antibody-Antigen Interactions.

First, a 2 minute baseline was acquired in PBS. A 300 μg/mL solution of a His-tagged maltose binding protein (MBP) fusion protein (MW=70 kDa) specific to IgG (MW=150 kDa) prepared in HEPES-NaCl with 10-20% glycerol, was diluted to the specified concentration with PBS and was injected for 10 minutes to immobilize the His-tagged protein antigen on the SPR sensor. This system was analyzed to compare the performance of the SPR sensor with a known biological system and correlated to other techniques. The excess of antigen was rinsed with PBS before acquiring a 5 minute baseline in PBS. Binding of IgG was detected by flowing increasing concentrations (5 nM to 1 μM) of the solution with an analysis time of 5 minutes for each concentration. A final rinsing step with PBS was accomplished. A 10 minute exposition to a saturated EDTA solution followed by a 10 minute period in a 100 mM copper sulfate solution was used for a complete regeneration of the antibody-antigen sensor, allowing at least two detection cycles for IgG on the same SPR sensor.

Real-Time Monitoring of the hDHFR Enzymatic Reaction.

The peptidomimetic monolayer binding His-tagged biomolecules was exposed for a period of 15 min to a 50 μg/mL PBS solution of His-tagged hDHFR, then rinsed with PBS. The SPR sensor with His-tagged hDHFR was placed in a UV/Vis cuvette, similar to a method developed by Knoll et al. (Xu et al., 2005. *Journal of the American Chemical Society* 127(38), 13084-13085). His-tagged hDHFR was obtained as previously reported (Volpato et al., 2007 *Journal of Molecular Biology* 373, 599-611). A negative control, consisting of the peptidomimetic-modified SPR sensor without hDHFR was exposed to buffer and rinsed to verify that the observed change in absorbance was due to immobilized His-tagged hDHFR and not to the surface itself. The enzymatic reaction catalyzed by hDHFR was monitored by UV/Vis spectrometry. The SPR sensors were immersed in a solution of 100 μM NADPH (cofactor) and 100 μM dihydrofolate (DHF, substrate) in 10 mM Tris buffer, pH=8.0, for 1 hour. The activity of the enzyme was measured by following the time course of the absorption ($\Delta A(t)$) at $\lambda$=340 nm due to consumption of NADPH and DHF, by subtracting the blank signal ($A_{blank}(t)$) and the initial absorbance of the solution (A(O)). The activity was confirmed for each sample of His-tagged hDHFR on the SPR sensor. 1 U of enzyme activity corresponds to conversion of 1 μmol substrate to product per min. Absorption spectra were recorded with a Cary 100 Bio UV/Vis spectrometer equipped with a liquid temperature control system running at 35° C. to be in the optimal condition for the enzymatic reaction to take place. After monitoring the activity, the SPR sensors were rinsed with buffer, 18.2 MΩ water and the His-tagged hDHFR was removed from the surface with a 0.5 M imidazole solution for 10 minutes. The abundantly rinsed surfaces were tested again for enzyme activity at 340 nm to show that no His-tagged hDHFR remained on the SPR sensor. Another rinse was performed with 18.2 MΩ water, followed by 10 minutes in 100 mM $CuSO_4$, then with His-tagged hDHFR to regenerate the surface. The enzymatic reaction was monitored to demonstrate the reusability of this immobilization strategy.

CD36 Peptide Ligands Screening.

The SPR sensors for screening small peptidic ligand binding to a recombinant soluble His-tagged CD36 functionalized surfaces were prepared as described above. Five ligands were investigated: EP80317, CP-2B(i), CP-3(iv), CP-2A(v) and DBG-178$_{(27)}$ with concentrations ranging from 30 μM to 100 nM except for EP80317. The latter was used for optimizing the system with solutions ranging from 1 mM to 100 nM. EP80317 (HAIC-2MeDTrp-DLys-Trp-D-Phe-Lys-NH$_2$) is a positive control of known activity, CP-2B(i) (His-DTrp-Aza-Leu-Trp-DPhe-Ala-NH$_2$) is a negative control, and CP-3(iv) (Ala-DTrp-Ala-AzaPhe-DPhe-Lys-NH$_2$), CP-2A(v) (His-DTrp-AzaGly-Trp-DPhe-Lys-NH$_2$) and DBG-178$_{(27)}$ (His-DTrp-Ala-azaTyr-DPhe-Lys-NH$_2$) are novel CD36 ligands (see PCT publication No. WO 08/154,738). Another negative control was accomplished by exposing the His-tagged hDHFR functionalized surface to the same concentration of CD36 peptidic ligand. Two different approaches were used to remove the His-tagged CD36-Cu complex from the SPR sensors: concentrated histidine solution or saturated EDTA solution.

Example 2

Binary Patterned Peptides (Heteropeptides) Tested in the Experiments Described Herein Several peptides were synthesized according to the procedure described in Example 1. Amino acids having different physico-chemical properties (polar, basic, acidic or hydrophobic) were selected to investigate the effect of different physico-chemical properties on various parameters of SPR sensing: surface concentration of the monolayer, the contact angle and the resistance to nonspecific adsorption. Hence, a polar amino acid, Ser (S), a basic amino acid, His (H), an acidic amino acid, Asp (D), and a hydrophobic amino acid, Leu (L). These represent the categories of physico-chemical properties encountered in natural and synthetic amino acids. Different types of series are investigated in the experiments described herein. First, a series of 3-MPA-H$_x$-D$_y$-OH amino acids, where, x is the number of His in the peptide and y is the number of Asp in the peptides. x and y were varied from 0-5 for both His and Asp, with a total number of amino acids kept constant at 5. The amino acids are arranged in blocks, as an example the peptide 3-MPA-H$_3$-D$_2$-OH (3-MPA-HHHDD-OH; SEQ ID NO:1) in which H$_3$ represents 3 His residues attached to the N-terminal linker 3-MPA and D$_2$ represents 2 Asp residues on the C-terminal end of the peptide. A second series of heteropeptides described herein is a combination of 3-MPA-A$_3$-B$_2$-OH, where A is either Leu, Ser, His, or Asp, and B is either Ser, His, or Asp. The other series of heteropeptides described herein have the following structure: 3-MPA-XXYYZZ-OH; 3-MPA-XYXYX-OH, 3-MPA-(XYZ)$_2$-OH and 3-MPA-X$_4$Y-OH, wherein X, Y and Z represent different amino acids.

Example 3

Determination of Bovine Serum Nonspecific Adsorption

Figure 1B:
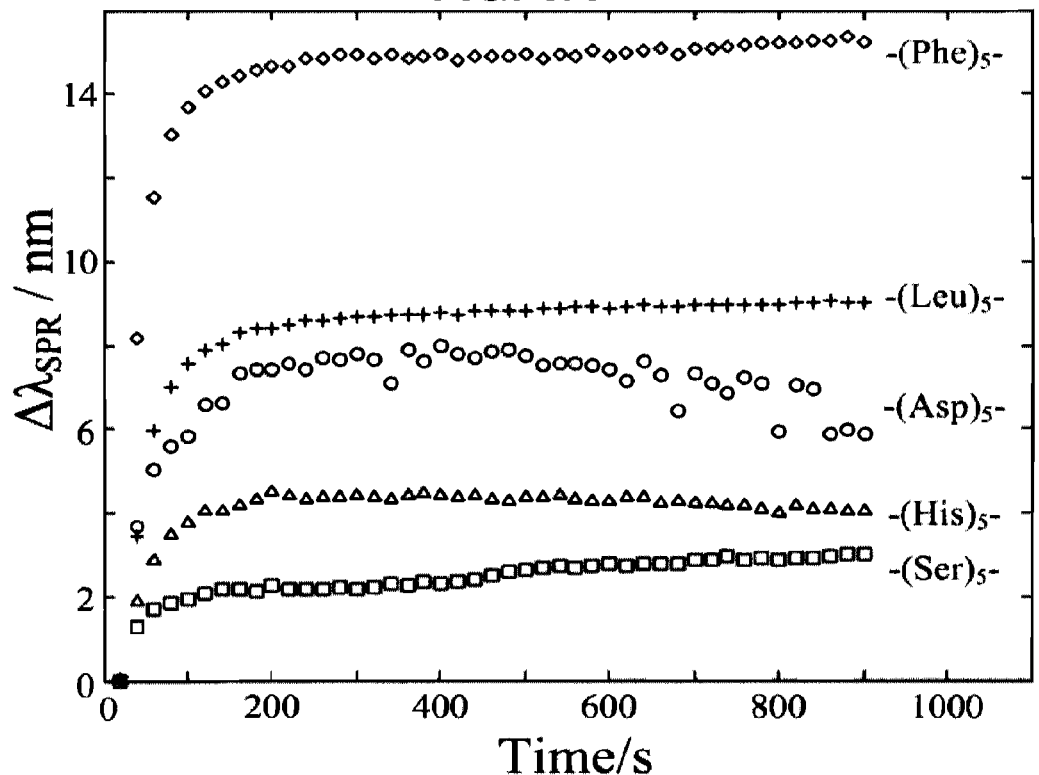
FIG. 1B shows a sensorgram demonstrating the nonspecific adsorption of bovine serum proteins on a self-assembled monolayer (SAM) of various homopeptides, namely 3-MPA-(Ser)$_5$-OH (SEQ ID NO:2), 3-MPA-(His)$_5$-OH (SEQ ID NO:3), 3-MPA-(Asp)$_5$-OH (SEQ ID NO:4), 3-MPA-(Leu)$_5$-OH (SEQ ID NO:5) and 3-MPA-(Phe)$_5$-OH (SEQ ID NO:6)

FIG. 1 shows the SPR response over time for the nonspecific adsorption of bovine serum (time=200-1200 s). The first part of the sensorgram is a reference measured while PBS is in contact with the surface of the SPR sensor covered with the 3-MPA-HHHDD-OH peptide. PBS is first injected over a period of 200 s in the SPR system. The SPR response is very stable as demonstrated during the 0 to 200 s time frame of the sensorgram depicted in FIG. 1A. After 5 minutes, PBS is replaced with adult bovine serum. The instant shift of signal is due to the refractive index of the bulk solution (the refractive index of serum is greater than the refractive index of PBS). This shift is unrelated to the nonspecific adsorption of proteins. The more progressive increase of $\lambda_{SPR}$ typical to a Langmuir-Blodgett model describing the evolution of interactions at a surface used to characterize the evolution of the nonspecific interaction with time. PBS buffer is then injected over the sensor to obtain a second reference, allowing the quantification of nonspecific proteins still attached at the surface of the sensor. A return to the initial $\lambda_{SPR}$ value (i.e., the value prior to bovine serum injection), as shown in FIG. 1A (1200 s to 1600 s time frame) is indicative of an efficient SAM that reduces nonspecific interactions. The stability of the signal (a less than 1 nm shift) shows that bovine serum minimally interacts with the surface of the SPR sensor in the presence of the 3-MPA-HHHDD-OH heteropeptide. In comparison, shifts of about 3 to about 14 nm were observed in the presence of various homopeptides (FIG. 1B).

Figure 2:
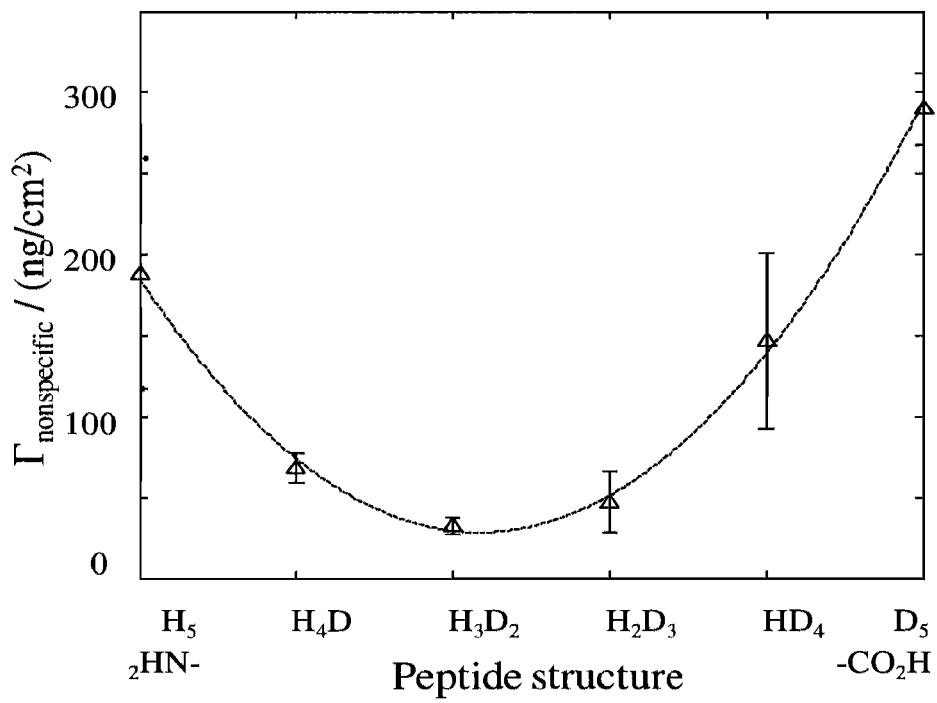
FIG. 2 shows a plot of nonspecific surface coverage for various binary patterned peptides and homopeptides. The nomenclature used is the following: $H_5$=3-MPA-HHHHH-OH (SEQ ID NO:3), $H_4D$=3-MPA-HHHHD-OH (SEQ ID NO:7), $H_3D_2$=3-MPA-HHHDD-OH (SEQ ID NO:1), $H_2D_3$=3-MPA-HHDDD-OH (SEQ ID NO:8), $HD_4$=3-MPA-HDDDD-OH (SEQ ID NO:9), and $D_5$=3-MPA-DDDDD-OH (SEQ ID NO:4)

The performance of 5-residue peptides comprising various combinations of His and Asp was assessed. The amount of nonspecific adsorption of proteins over these SAMs was determined using the assay described above for the 3-MPA-HHHDD-OH peptide (FIG. 1). A plot of nonspecific surface coverage in function of the structure of the peptides is shown in FIG. 2. The reduction of nonspecific interactions is better for peptides comprising a combination of two different amino acids as compared to homopeptides, indicating that heteropeptides have an increased ability of reducing nonspecific adsorption relative to corresponding homopeptides.

Example 4

Characterization of the Nonspecific Adsorption Inhibitory Properties of Various 3-MPA-A$_3$-B$_2$-OH Heteropeptides The formation of monolayers on Au was measured to ensure that the peptide monolayers are indeed binding to the SPR sensor. The surface concentration of the monolayer provides a measurement of the number of molecules per square cm (i.e. the density of the monolayer at the surface). The surface concentration ($\Gamma$) of peptide-like self-assembled monolayers (SAMs) was characterized with the measurement of the SPR response before the formation of the SAMs and after their formation on the Au surface of the SPR sensor. The difference of SPR wavelength ($\lambda_{SPR}$) between these two measurements increases with the increasing surface concentration of the SAMs following the equation proposed by Jung et al. (Jung, L. S. et al. *Langmuir* 1998, 14: 5636):

$$\Gamma = \rho(-0.5/_d)\ln(1-(\Delta\lambda_{SPR} m^{-1}(\eta_{SAM}-\eta_{PBS})^{-1})) \quad \text{(eq. 1)}$$

Peptide-like SAMs form dense monolayers, characterized by a surface density of varying between $(0.125-0.441)*10^{14}$ molecules/cm$^2$ (Table 1) reaching values similar to those previously recorded for homopeptide SAMs and single amino acid SAMs (Bolduc, O. R. et al. *Anal. Chem.* 2009, 81: 6779; Bolduc, O. R. and Masson, J. F. *Langmuir* 2008, 24: 12085). Values for the sensitivity, refractive Index, penetration depth were Identical to the values previously used by Bolduc et al (Bolduc, O. R. et al. *Anal. Chem.* 2009, 81: 6779; Bolduc, O. R. and Masson, J. F. *Langmuir* 2008, 24: 12085). Table 1 shows that no trend was observed from the surface concentration with the composition of the peptide SAM.

The amount of non-specifically bound proteins at the surface of binary patterned peptide SAMs was obtained by recording the change of $\lambda_{SPR}$ observed when undiluted adult bovine serum having a protein concentration superior to 70 mg/ml is put into contact with the SPR sensors. Table 1 shows that peptide SAM adsorbed from 23 ng/cm$^2$ to 79 ng/cm$^2$ of nonspecific proteins. These values are lower than those measured in other types of monolayers, which typically range between 100 to 1000 ng/cm$^2$ (Luppa, P. B. et al. *Clin. Chim. Acta* 2001, 314: 1); Masson, J. F. et al. *Talanta* 2005, 67: 918; Masson, J. F. et al. *Anal. Bioanal. Chem.* 2006, 386: 1951; Bolduc, O. R. et al. *Anal. Chem.* 2009, 81: 6779; Bolduc, O. R. and Masson, J. F. *Langmuir* 2008, 24: 12085). As demonstrated below, this improvement is significant enough to allow direct detection assays in complex matrices, thus reducing the time and cost of such assays.

Advancing contact angles using phosphate buffer saline (PBS) showed that the peptide SAMs are hydrophilic, with contact angles ranging from 37.8° to 52.3°, indicating that the peptide monolayers are wetting the surface of the SPR sensor.

Table I classifies the different peptides from the most to the least resistant monolayers to nonspecific adsorption of serum proteins. This classification highlights the relationship between the structure of the peptides and their performance as monolayers improving nonspecific adsorption. While peptides with Leu exhibit good performance, a more polar core, such as His and Ser, exhibits even better performance especially when linked to Asp residues at the C-terminal end. Furthermore, the presence of aspartic acid at the C-terminal end would also potentially lead to better attachment of a recognition molecule (e.g., antibody, enzyme, DNA, aptamer or others) through NHS-ester chemistry on the COOH groups of the Asp residues, an effect also expected for peptides having other acidic amino acids (e.g., glutamic acid) at the C-terminus.

TABLE I

Surface density ($\Delta\Gamma_{SAM}$), nonspecific adsorption ($\Delta\Gamma_{nonspecific}$) and contact angle in PBS ($\theta_{C\_PBS}$) of various peptide SAMs.

| peptide | $\Delta\Gamma_{SAM}\ 10^{15}$ molecule/cm$^2$ | $\Delta\Gamma_{nonspecific}$ ng/cm$^2$ | $\theta_{C\_PBS}$ (°) | SEQ ID NO: |
|---|---|---|---|---|
| 3-MPA-SSSDD | 0.441 | 23 | 38.8 | 19 |
| 3-MPA-HHHDD | 0.230 | 32 | 37.8 | 1 |
| 3-MPA-LLLDD | 0.352 | 35 | 52.3 | 20 |
| 3-MPA-LLLSS | 0.255 | 39 | 32.6 | 21 |
| 3-MPA-LLLHH | 0.296 | 45 | 41.4 | 22 |
| 3-MPA-HHHSS | 0.125 | 48 | 39.9 | 23 |
| 3-MPA-DDDHH | 0.279 | 56 | 46.4 | 24 |
| 3-MPA-DDDSS | 0.311 | 69 | 51.2 | 25 |
| 3-MPA-SSSHH | 0.301 | 79 | 40.0 | 26 |

Results are an average of four replicates

Example 5

Figure 3:
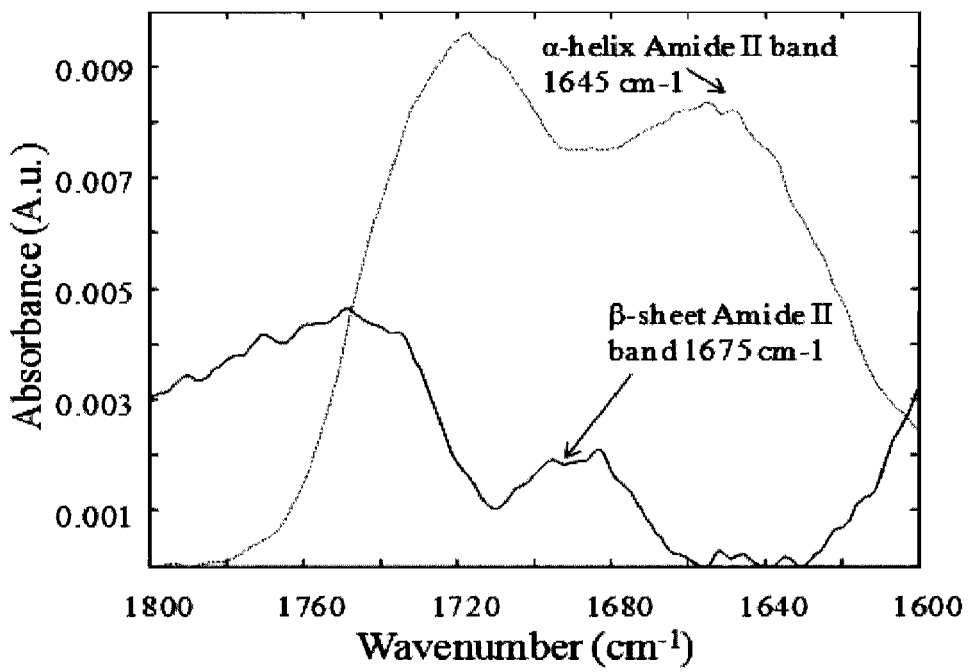
FIG. 3 shows the determination of the β-sheet or α-helix configuration of a binary patterned peptide SAM using Fourier transform infrared (FT-IR) spectroscopy.

FT-IR Determination of the Structure of the Heteropeptides at the Surface of the SPR Sensor The 3D structure of the peptides as SAMs is observed with the amide band visible in FT-IR. Peptides adopting an α-helix configuration are showing a strong amide band at 1645 cm$^{-1}$, while peptides auto-assembling in the β-sheet configuration leads to a shifted amide at 1675 cm$^{-1}$. Every peptide structure investigated in Table 1 adopted an α-helix configuration except for 3-MPA-HHHDD-OH, as shown in FIG. 3. FIG. 3 shows the α-helix configuration of one of the peptides (for clarity purposes, only one α-helix configuration spectrum is depicted), and the β-sheet configuration of 3-MPA-HHHDD-OH.

Capillary electrophoresis was performed to determine if this difference of configuration is due to the global charge of the peptide. Calibration runs were performed demonstrating that the difference of global charge between 3-MPA-HHDDD-OH, 3-MPA-HHHDD-OH and 3-MPA-HHHHD-OH is almost negligible (their global charge is about −1), thus demonstrating that the different configuration observed in FT-IR is not caused by an effect of charge of the 3-MPA-HHHDD-OH peptide.

The synthesis of 3-MPA-HHHDD-OH and the formation of the SAM on the gold-coated SPR surfaces were assessed using FT-IR. Both spectra of His and Asp are visible in the spectra obtained for 3-MPA-HHHDD-OH. The spectrum of 3-MPA shows a weak band at 2580 cm$^{-1}$ corresponding to the S—H stretch, also observed in the spectrum of the peptide. The strong signal of C=O stretch at 1763 cm$^{-1}$ confirms the presence of COOH groups at the surface of the SAMs. The COOH groups are typically used to attach the biorecognition molecules through their free amines, thus allowing the development of a biosensor.

Example 6

Preparation of a Biosensor Using the 3-MPA-HHHDD-OH Peptide

In order to demonstrate the efficiency of binary patterned peptide SAMs to immobilize biorecognition molecules, such as antibodies, in the construction of an affinity biosensor, an EDC/NHS solution was reacted with the free COOH of the 3-MPA-HHHDD-OH peptide. EDC/NHS activated the COOH group and allowed the attachment of the antibody specific to IgG (anti-IgG) via the free amines of the antibody. The excess of NHS-ester activated COOH was deactivated with an ethanolamine solution. Following stabilization in PBS, a solution containing an IgG was injected on the SPR biosensor. Thereafter, PBS was injected again to check the reversibility of the interactions between anti-IgG and IgG.

Figure 4A:
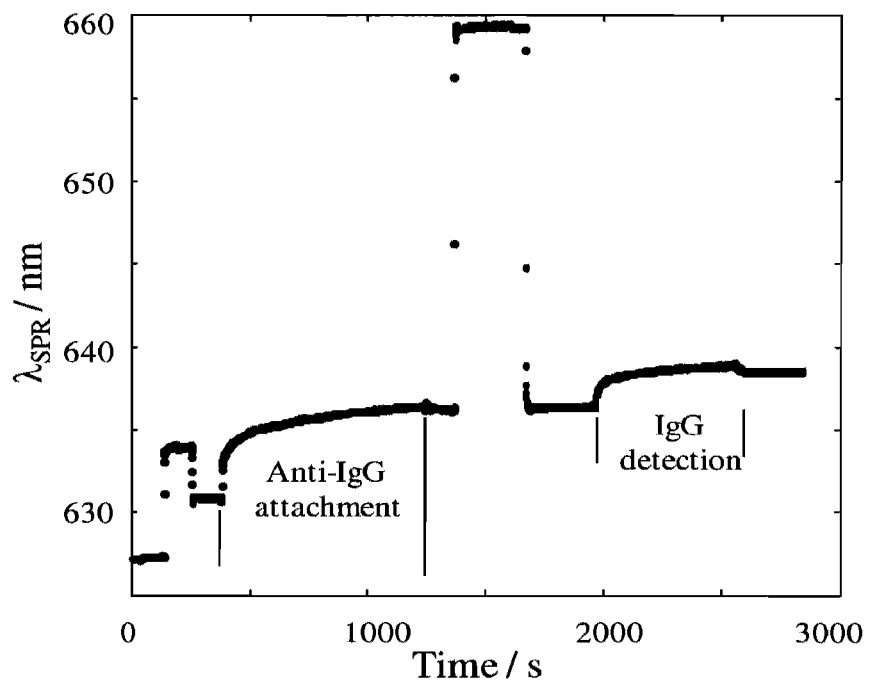
FIG. 4A shows a sensorgram for the fabrication of an IgG-specific biosensor. This SPR sensor uses the 3-MPA-HHHDD-OH monolayer. The order of the different steps is: water, EDC/NHS, PBS, anti-IgG, PBS, ethanolamine, PBS, IgG, PBS.
Figure 4B:
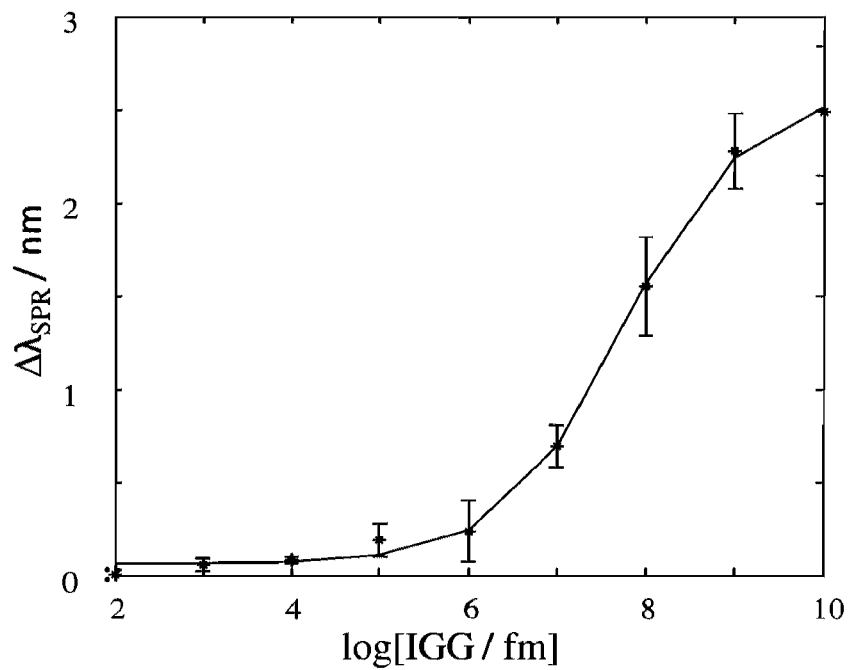
FIG. 4B shows a calibration curve of IgG in PBS, the full line represents the theoretical values predicted by the Langmuir equation. The concentration of IgG is given in a logarithmic scale in femtomolar (fM, $10^{-15}$ M)

The SPR response was recorded for each step in order to demonstrate the reaction occurring at the surface (FIG. 4, left panel). The interaction between IgG and anti-IgG is not fully reversible in the time scale of the experiment, since the signal did not return to the initial baseline values following the last exposition to PBS (which may be explained by the high affinity of the IgG/anti-IgG interaction). The calibration curve of IgG using 3-MPA-HHHDD-OH with anti-IgG immobilized, shows the behavior of a Langmuir isotherm (FIG. 4, right panel). The x-axis represents the logarithm of IgG concentration, while the y axis represents the SPR response. A linear domain of SPR response is observed within the nM range of concentration (from about 6 to 9 in the concentration logarithmic scale). This domain loosely delimits the concentration of interest that could be determined using such devices. The SPR response observed outside this domain is saturated for superior concentration and lower than the binding constant for inferior concentrations. This leads to a limit of detection of 3 pM, similar or lower than IgG detection with other biosensors.

Example 7

Detection of MMP-3 in Saline and Complex Media

Figure 5A:
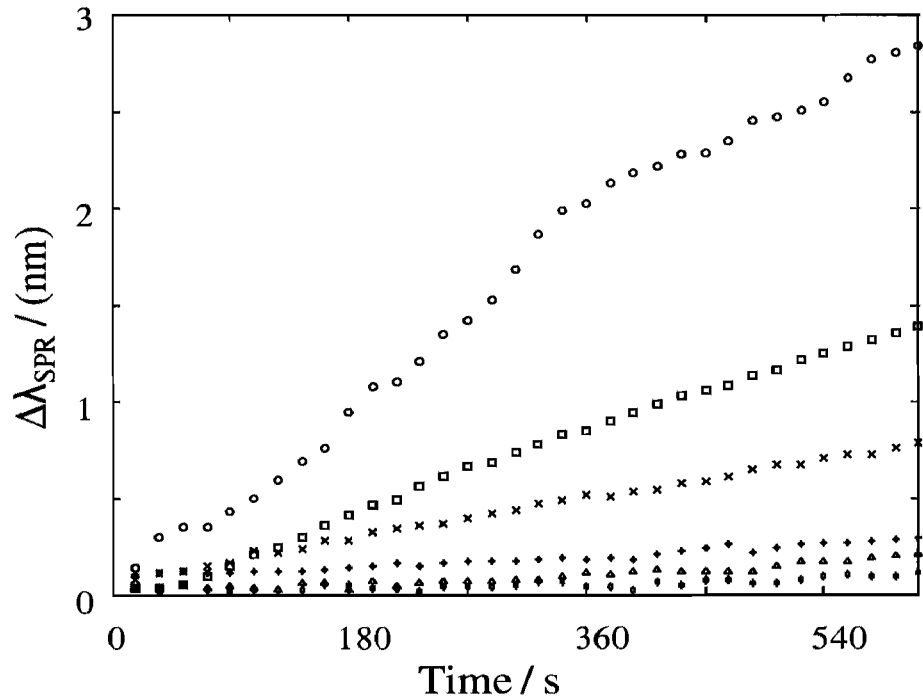
FIG. 5A shows an overlap of sensorgrams for the detection of different concentrations of MMP-3 in PBS. The concentrations detected are 0.5 nM, 1 nM, 6 nM, 12.5 nM, 25 nM and 50 nM. The uppermost group of data points ('o') correspond to 50 nM, and the lower groups of data points correspond to the lower concentrations in descending fashion (e.g., '□' for 25 nM, 'x' for 12.5 nM, etc.) to the lowest concentration of 0.5 nM (data points represented by symbol of an open square intersected with a vertical line).
Figure 5B:
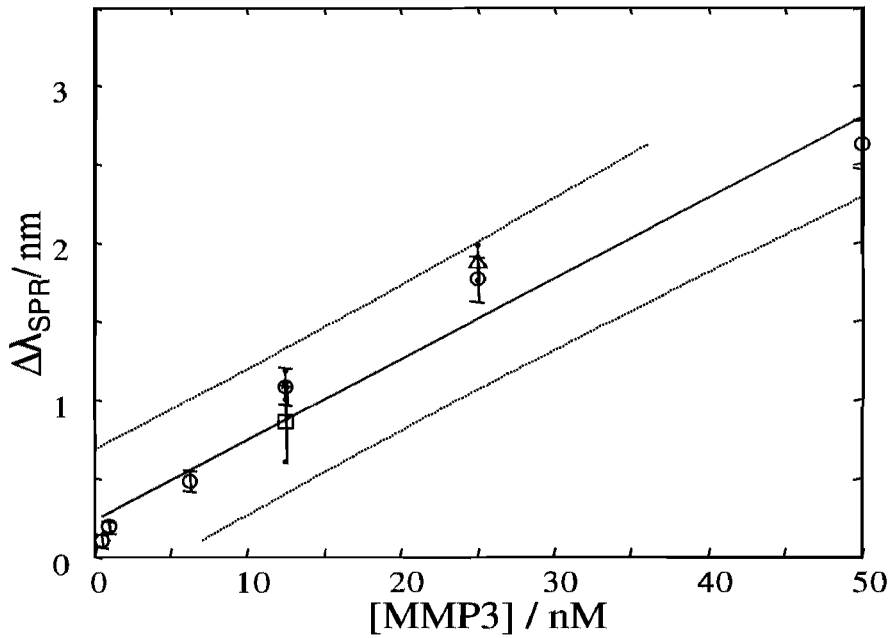
FIG. 5B shows a calibration curve of MMP-3 in PBS, with labels 'o' (n=3; number of replicate measurements at each concentration). The quantification of MMP-3 in complex matrices is represented with: 'Δ' for the detection of 25 nM MMP-3 in full bovine serum; '*' for the detection of 12.5 nM in full bovine serum; and '□' for the detection of 12.5 nM in a 1/1 mixture of bovine serum/PBS.

The SPR sensor was prepared using a procedure similar to that described above for IgG, except that anti-human MMP-3 was used as the recognition biomolecule for human MMP-3. The sensorgrams for different concentrations of MMP-3 showed that the intensity of the SPR responses was proportional to the concentration of MMP-3 in PBS (FIG. 5). The SPR response in function of MMP-3 concentration was linear over the concentrations of MMP-3 probed. This allows the quantification of MMP-3 over a targeted domain of concentration comprised between about 1 nM and 50 nM, with a detection limit at near- or sub-nanomolar. The correlation coefficient ($R^2$) for this calibration curve was 0.96, indicative of a strong linear relationship between the SPR response and the concentration of MMP-3.

In order to demonstrate the efficiency of 3-MPA-HHHDD-OH to reduce the level of nonspecific interactions with the surface of a biosensor, detection assays of an enzyme were performed in full bovine serum. MMP-3 was used as an analyte for its potential as an indicator of pathologic conditions such as invasive cancer and kidney failure among others.

The exposition of the SPR sensor to serum free of MMP-3 showed little response due to nonspecific interactions. This pre-exposition to blank bovine serum for two minutes measured the nonspecific interactions of 3-MPA-HHHDD-OH with the sample matrix. This also demonstrates that the MMP-3 specific biosensor does not interact with the nonspecific proteins present in blood serum. The values of nonspecific interactions obtained for those devices are similar to those presented in Table 1 for 3-MPA-HHHDD-OH without the anti-MMP-3 attached to the surface of the SPR sensor. This confirms that nonspecific interaction is negligible on binary patterned peptide SAMs with or without antibody derivation.

Figure 6:
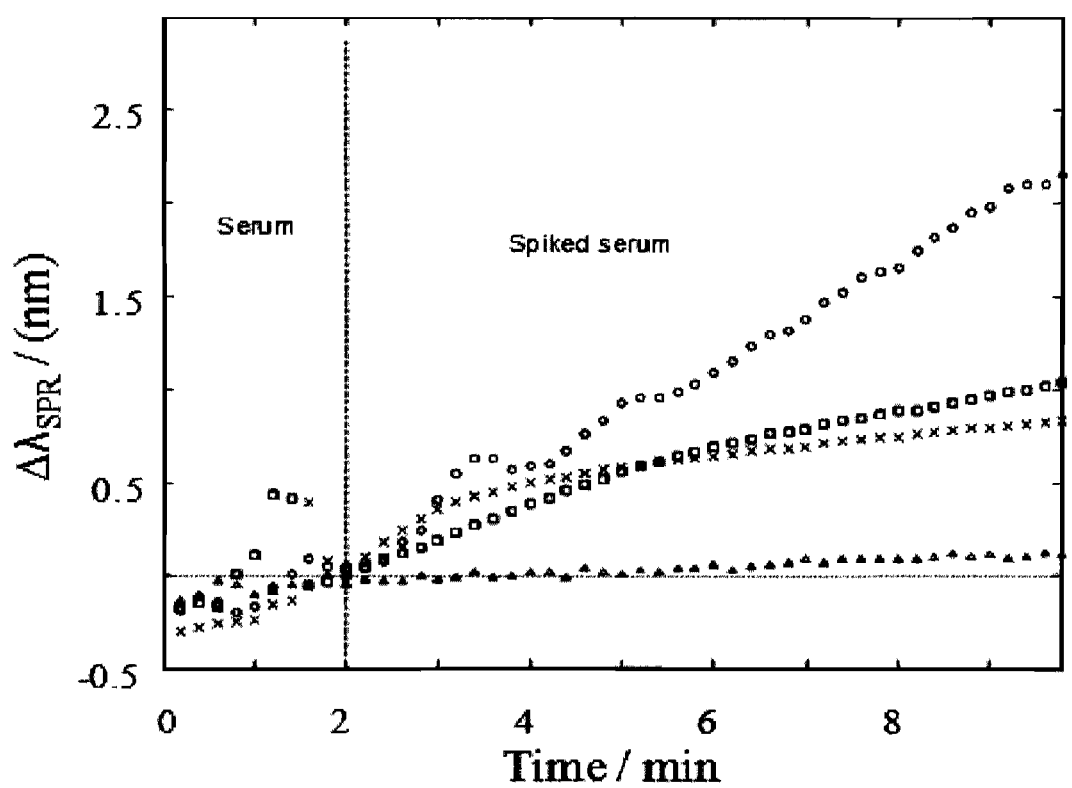
FIG. 6 shows detection assays of human MMP-3 in complex matrices. This enzyme was spiked in bovine serum (exempt of human MMP-3) at 25 nM for a first assay, with labels 'o'. A 1:1 dilution with bovine serum, labels '□' and with PBS, labels 'x', brought this concentration to a level of 12.5 nM. A blank assay, labeled 'Δ', demonstrates that the shift of the SPR response observed for the three (3) other sensorgrams is due to specific interactions of MMP-3 with anti-MMP-3.

As shown in FIG. 5, the detection of 25 nM MMP-3 in bovine serum results in a SPR response statistically identical to that measured with 25 nM MMP-3 in saline solution (PBS), demonstrating that the serum does not interfere with the detection of MMP-3, and thus that MMP-3 may be detected in a complex biological matrix using a heteropeptide-based SAMs. The similar SPR response observed with 12.5 nM MMP-3 in serum and in a 1:1 PBS/serum mixture again suggests that nonspecific protein adsorption in undiluted serum has a minimal influence on the measured SPR response. FIG. 6 shows the SPR response of 25 nM MMP-3 in serum, which was significantly different to the response of a blank serum sample. The SPR response of 12.5 nM MMP-3 in either serum or 1:1 PBS/serum mixture was very similar. These are also significantly greater than the response observed for the blank serum. The average values for three independent measurements with different sensors (n=3) of the SPR response observed for the various detection of MMP-3 in bovine serum are reported in the calibration curve presented in FIG. 5, right panel. These assays demonstrated the efficiency of heteropeptide-based SAMs immobilized on the SPR biosensors for detection assays in complex analytical matrices.

Example 8

Characterization of the Nonspecific Adsorption Inhibitory Properties of Other Types of Heteropeptides The potential of seven peptides structured as: 3-MPA-XX-YYZZ-OH, 3-MPA-XYXYX-OH, 3-MPA-(XYZ)$_2$-OH and 3-MPA-X$_4$Y-OH in reducing nonspecific adsorption of proteins was investigated. A variation of nonspecifically adsorbed proteins was observed with the different configurations of peptide SAM (Table II). The peptide monolayers in the general form of 3-MPA-XXYYZZ-OH, 3-MPA-DHDHD-OH (SEQ ID NO:27) and 3-MPA-GGGGD-OH (SEQ ID NO:28) showed low resistance to nonspecific adsorption, with protein coverage greater than >100 ng/cm$^2$. However, a significant improvement was observed for both peptides in the form of 3-MPA-(XYZ)$_2$-OH, which decreased nonspecific adsorption to approximately 12 to 17 ng/cm$^2$. A reduction in nonspecific adsorption by factor of 2 is obtained for 3-MPA-LHDLHD-OH (SEQ ID NO:29) relative to the nonspecific adsorption of binary peptide SAM (see Table I above). This value approaches the detection limit of SPR (nearly 1 ng/cm$^2$).

Peptides adopt secondary conformation, which plays a significant role in their biological activity. For peptides in solution, the secondary conformation is measured with CD, while peptides immobilized on a surface can be analyzed with mid-IR spectroscopy of the amide bands (Duevel, R. V., Corn, R. M., 1992. *Analytical Chemistry* 64(4), 337-342; Sakurai, T. et al., 2006. *Journal of Peptide Science* 12(6), 396-402). As listed in Table II, the secondary structure of most peptides adopted an α-helical conformation, with the exception of 3-MPA-DSDSD-OH, which adopted an extended conformation. As noted above, most peptides in the form of 3-MPA-peptide-OH adopt an α-helical conformation. Generally, mid-IR and CD agreed in the determination of the structures on surfaces and in solution, with the exception of one peptide. 3-MPA-SHDSHD-OH (SEQ ID NO:33) exhibited an α-helical conformation on surfaces as assessed by FT-IR and an extended conformation in solution as assessed using CD, suggesting that this peptide may adopt a different structure in solution than as a monolayer. No relationship between structure and nonspecific adsorption could be established.

Because of its good resistance to nonspecific adsorption, peptide 3-MPA-LHDLHD-OH was used in the studies described hereinafter.

TABLE II

Properties of peptide SAMs: nonspecific adsorption and secondary structure

| | | Secondary Structure | |
|---|---|---|---|
| Sequence | $\Delta\Gamma_{nonspecific}$ (ng/cm$^2$) | FT-IR (SAM) | CD (solution) |
| 3-MPA-LLHHDD-OH (SEQ ID NO: 30) | 174 ± 120 | α | α |
| 3-MPA-GGHHDD-OH (SEQ ID NO: 31) | 149 ± 100 | α | α |
| 3-MPA-DHDHD-OH (SEQ ID NO: 27) | 274 ± 109 | α | α |
| 3-MPA-DSDSD-OH (SEQ ID NO: 32) | 34 ± 31 | extended | extended |

TABLE II-continued

Properties of peptide SAMs: nonspecific adsorption and secondary structure

| Sequence | $\Delta\Gamma_{nonspecific}$ (ng/cm$^2$) | Secondary Structure FT-IR (SAM) | CD (solution) |
|---|---|---|---|
| 3-MPA-LHDLHD-OH (SEQ ID NO: 29) | 12 ± 11 | α | α |
| 3-MPA-SHDSHD-OH (SEQ ID NO: 33) | 17 ± 14 | α | extended |
| 3-MPA-GGGGD-OH (SEQ ID NO: 28) | 218 ± 65 | α | α |

Example 9

Synthesis and Characterization of Peptidomimetic Monolayers Binding His-Tagged Proteins The peptidomimetic compounds were produced in large amount (hundreds of mg) and stored in an opaque and sealed container at room temperature. They were used over a period of 30 days without any change in the analytical signal. Peptides exhibit a good absorption signature in the mid-IR domain. Thus, the reactions performed on the SPR substrates were followed using FT-IR as a convenient way to rapidly obtain information about the composition of the peptidomimetic monolayer at the surface of a gold-coated sensor. Every spectral acquisition was preceded by the acquisition of a blank measurement with a bare gold-coated slide. The amide I band is of primary importance in the analysis of a peptide-based self-assembled monolayer to determine the secondary structure of the peptide on the SPR sensor. The amine I band for 3-MPA-LHDLHD-OH is located at 1645 cm$^{-1}$ typical for an α-helix. The C=O stretch of the carboxylic acid functional groups of the aspartic acid were observed at 1720 cm$^{-1}$ and, disappeared once coupled with Nα,Nα-bis(carboxymethyl)-L-lysine hydrate using EDC/NHS chemistry. This reaction was confirmed with FT-IR, with the appearance of two bands at 1670 and 1740 cm$^{-1}$ also observed on the spectra of pure Nα,Nα-bis(carboxymethyl)-L-lysine hydrate. The XPS spectrum of the peptidomimetic monolayer chelated with copper exhibited the Cu$_{2p}$ band at 934.07 eV confirming the presence of copper at the surface of the sensors. The relative peak areas observed for sulphur, nitrogen, carbon and oxygen correspond to the values expected for this SAM. The XPS response corresponding to Au and Cu indicate a strong presence of these two metals. Other metals such as Co or Ni can be used for His-tagged protein binding, the most common being Ni. Thus, Ni was also tried with the current peptidomimetic monolayer, which in this case did not appear on the XPS spectrum after exposure of the peptidomimetic monolayer to Ni. Copper-functionalized surfaces were used thereafter.

Example 10

K$_D$ Determination for an Antigen-Antibody System

Surface chemistry allowing effective regeneration of their sensitive surface is of great interest. The lifetime of the sensor template can be extended, useful for some applications where the sensor is expensive to fabricate. The immobilization of His-tagged proteins constitutes a major advantage for biosensors fabrication. Many proteins are produced with hexa-histidine tags to enable easy and efficient purification. Therefore, this approach has been exploited to immobilize proteins on biosensors (Blankespoor, R. et al., 2005. Langmuir 21(8), 3362-3375; Keller, T. A. et al., 1995. Supramolecular Science 2(3-4), 155-160; Kröger, D. et al., 1999. Biosensors and Bioelectronics 14(2), 155-161; Tinazli, A. et al., 2005. Chemistry—A European Journal 11(18), 5249-5259), and is similar to resins commonly used to purify proteins. The peptidomimetic monolayer was designed to bind His-tagged biomolecules. A simple system involving the complexation of a His-tagged antigen on the peptidomimetic monolayer immobilized on the SPR sensors was used measure the affinity of a specific antibody, and thus demonstrate the ability of the system to monitor protein-protein interactions. The dissociation constant (K$_D$) for this antigen-antibody system was determined using the Langmuir isotherm model (1).

$$\frac{1}{\Delta\lambda_{SPR}} = \frac{1}{K_D \Delta\lambda_{SPR_{MAX}}} \frac{1}{[IgG]} + \frac{1}{\Delta\lambda_{SPR_{MAX}}} \quad (1)$$

Figure 8A:
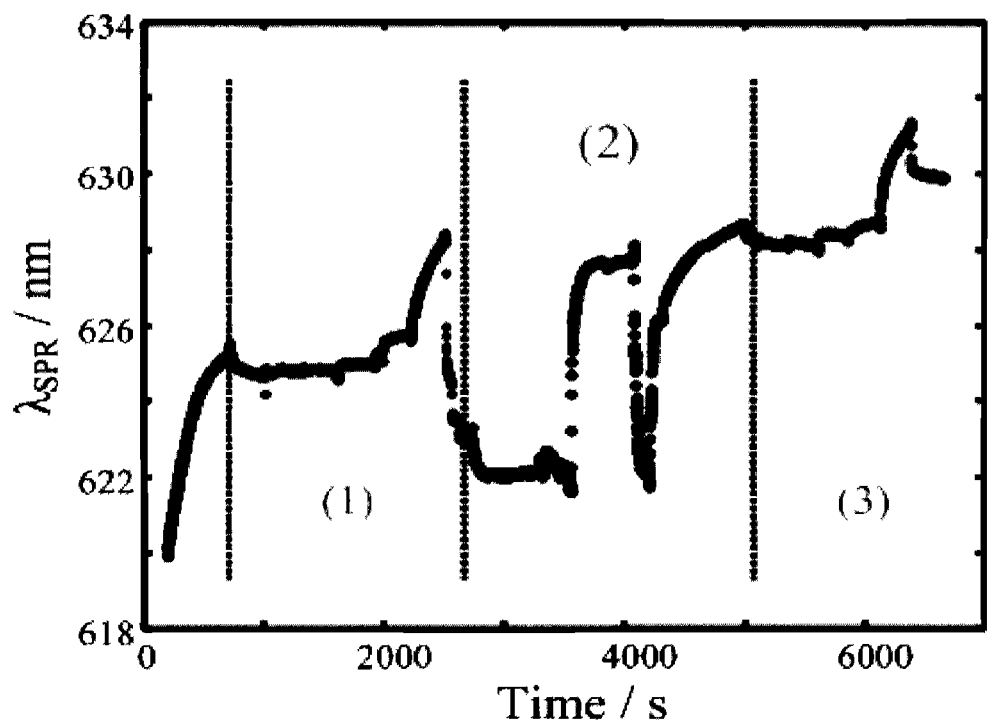
FIGS. 8A and 8B show SPR sensorgrams of two quantifications (steps 1 & 3) of IgG with a His-tagged fusion protein immobilized to the SPR sensor. Online regeneration of the sensor (step 2) was performed using a concentrated EDTA solution.
Figure 8B:
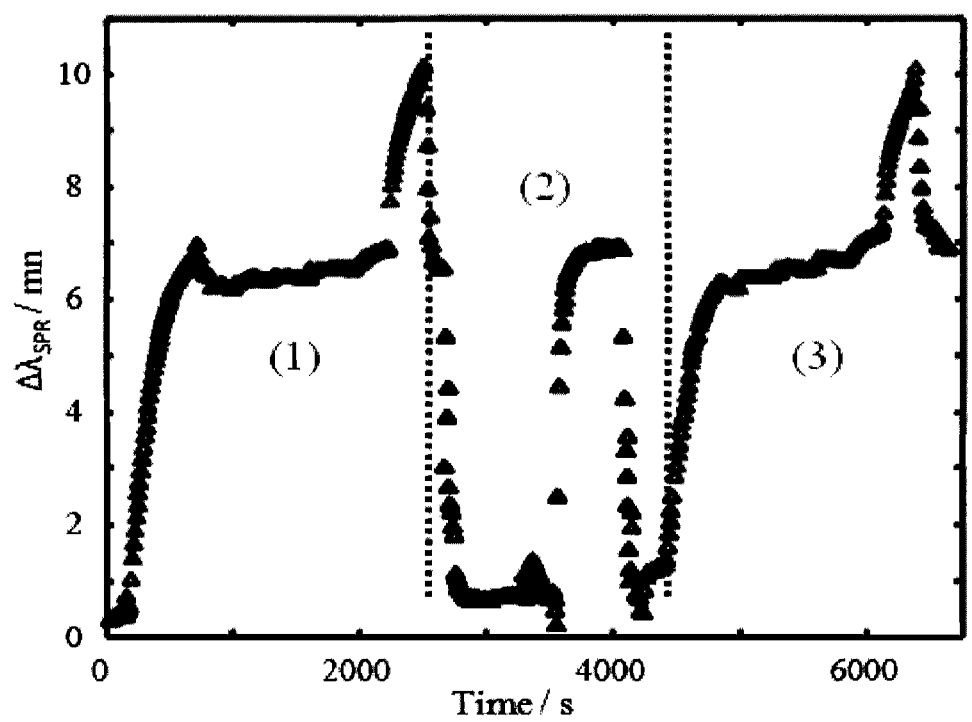

By plotting the inverse of the change of the SPR signal ($\Delta\lambda_{SPR}^{-1}$) in function of the inverse of the concentration of IgG ([IgG]$^{-1}$), K$_D$ is obtained by dividing the slope by the y-intercept of this graph (1/$\Delta\lambda_{SPRmax}$; SPR signal at saturation). FIG. 8 shows the functionalization, detection, regeneration and detection of a His-tagged Ag/Ab system. Here, regeneration of the SPR sensor was accomplished using extensive rinsing (the volume of rinsing is more than 100 times the volume of the fluidic cell) with concentrated histidine, imidazole or ethylene diaminetetraacetic acid (EDTA) solutions, allowing multiple measurement cycles per sensor. The SPR shifts observed for the second detection cycle were within range of the first detection cycle. Equation 1 allowed the determination of K$_D$ for this system at 9.6×10$^{-9}$ M. This value is within the typical range for an antigen-IgG system.

Example 11

Preservation of Enzyme Activity with Immobilized His-Tagged Human Dihydrofolate Reductase (hDHFR)

Figure 9:
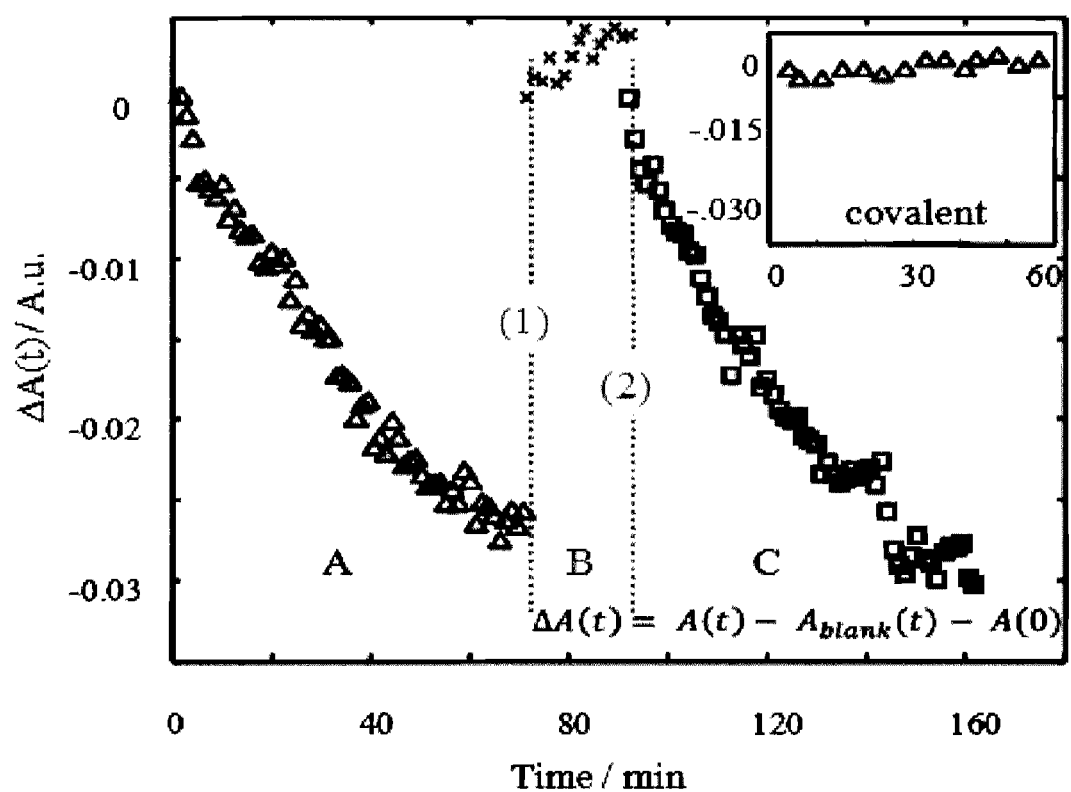
FIG. 9 shows the real-time monitoring of the enzymatic reaction for human dihydrofolate reductase (hDHFR)-Histag immobilized on the peptidomimetic monolayer. First, the measurement of the enzyme activity (step A) showed a decrease in absorbance due to the consumption of the reactants. Then, a wash with imidazole (step 1 not shown) was performed, which resulted in absence of enzymatic activity (step B). The regeneration of the surface (step 2 not shown) was followed by the second measurement of the enzyme activity (step C). Inset: enzyme activity measured for 60 minutes with hDHFR covalently immobilized on SPR sensors using EDC/NHS chemistry. Each data point represents the average of five measurements.

EDC/NHS couples the carboxylic acids of the monolayer with primary amines available on proteins in a non-discriminatory fashion. This results in the possibility of reacting primary amines essential for biological activity. For example, difficulty was encountered when immobilizing active hDHFR on SPR sensors with EDC/NHS coupling. The immobilized enzyme demonstrated no affinity for its substrate as observed with the measurement of the activity with UV/Vis spectroscopy and substrate binding with SPR. Monitoring the absorption band at 340 nm is a convenient way to measure the DHFR-catalyzed consumption of DHF (substrate) and NADPH (cofactor) in solution because their added molar absorptivity at this wavelength is greater than that of the reaction products. Thus, the measurement of the change in absorption during the conversion of the reactants into products, monitors the enzymatic activity. The control of enzyme deactivation using EDC/NHS chemistry was performed with this method. The covalent immobilization of hDHFR performed on 16-mercaptohexadecanoic acid (16-MHA) using EDC/NHS chemistry led to inactivation of the enzyme (FIG. 9—inset). The absorbance was invariable for hDHFR covalently immobilized to MHA, indicating that the enzyme was inactive on the surface. Trials with the peptide monolayer and EDC/NHS immobilization chemistry also yielded inactive hDHFR. Controls using the same reagents (MHA or peptide mixed with EDC/NHS) with hDHFR in solution gave the same results, suggesting that the inactivation is due to the reaction with EDC/NHS but not necessarily to the surface-immobilization per se.

In contrast with those results, immobilizing His-tagged hDHFR on the peptidomimetic monolayer allowed to retain the activity of the enzyme. This is observed by a consumption of the reactants (NADPH and DHF), decreasing the absorbance measured at $\lambda=340$ nm (FIG. 3). According to the absorption coefficient ($\Delta\epsilon=12.8$ mM$^{-1}$ cm$^{-1}$), the measured slope (5.7*10 Abs/min) corresponded to an activity of $4.4\pm0.8*10^{-5}$ U. The specific activity of His-tagged hDHFR previously determined in presence of saturating reactants was 8.5 U/mg. Thus, the activity measured on the surface corresponded to $5\pm0.9$ ng (n=4) of fully active hDHFR. A negative control, consisting of the peptidomimetic monolayer-modified SPR sensor without hDHFR, showed no significant absorbance fluctuations, indicating that the SPR components do not modify the absorbance of the reaction mixture. The fraction of active enzyme on the surface cannot be determined, because the activity measured for the enzyme immobilized on the surface of the SPR is a factor of the activity of the enzyme (as for the enzyme in solution) and the time required for the products to diffuse in the light beam of the UV-Vis (not a factor for the enzyme in solution). Thus, it can be concluded that hDHFR is active when immobilized on the peptidomimetic monolayer binding His-tagged biomolecules.

The SPR sensors were regenerated by displacing Cu with a 0.5 M imidazole solution. hDHFR was removed from the surface and washed away, thus showed no activity upon monitoring by UV-Vis (FIG. 9). The steady absorbance value indicates that the displacement step was efficient, leaving no hDHFR immobilized at the surface of the sensors. This displacement step was also accomplished using a concentrated EDTA solution or 1 M histidine with similar results (n=4 for each solution). After functionalizing the surface once more with copper and His-tagged hDHFR, the surface held active enzyme once again, demonstrating the possibility of regenerating the SPR sensors. The SPR response measured during each cycle of immobilization of His-tagged hDHFR revealed that 50-75 ng/cm$^2$ of enzyme is present on the surface. Negative controls with no enzyme showed no activity. The average variation of the absorbance value over 60 minutes for four sensors regenerated with imidazole was determined to be $-0.034\pm0.006$ (n=8) demonstrating the ability to regenerate the sensors with the peptidomimetic monolayer binding His-tagged biomolecules without altering the surface properties.

The combination of the appropriate peptide chemistry and capacity for metal-based affinity thus provides a low-background, highly-reusable surface for immobilization of biomolecules that are sensitive to EDC-NHS chemistry.

Example 12

Figure 10A:
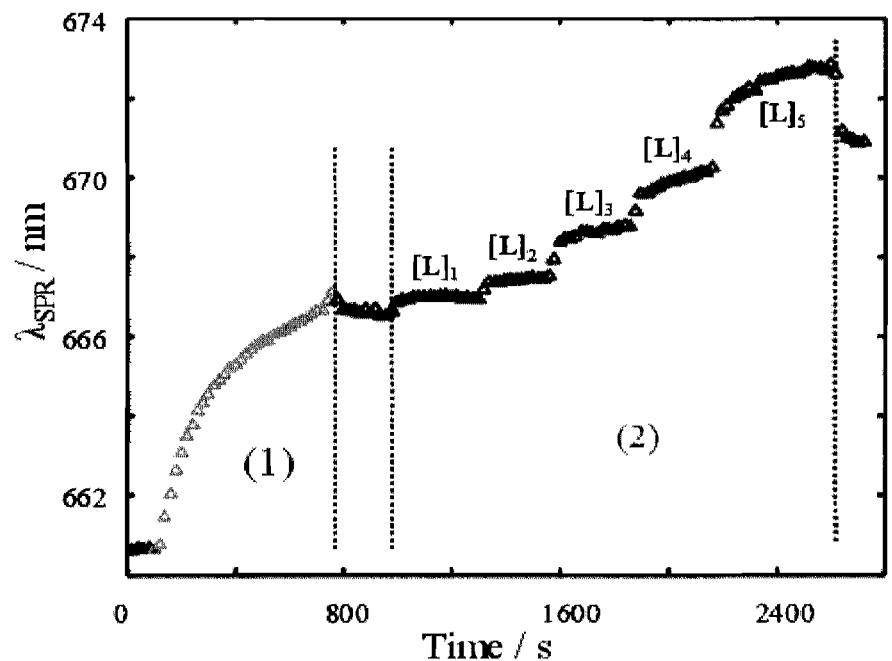
FIG. 10A shows a SPR sensorgram of CD36 functionalized (step 1) sensor exposed to increasing concentrations of EP80317 (step 2)
Figure 10B:
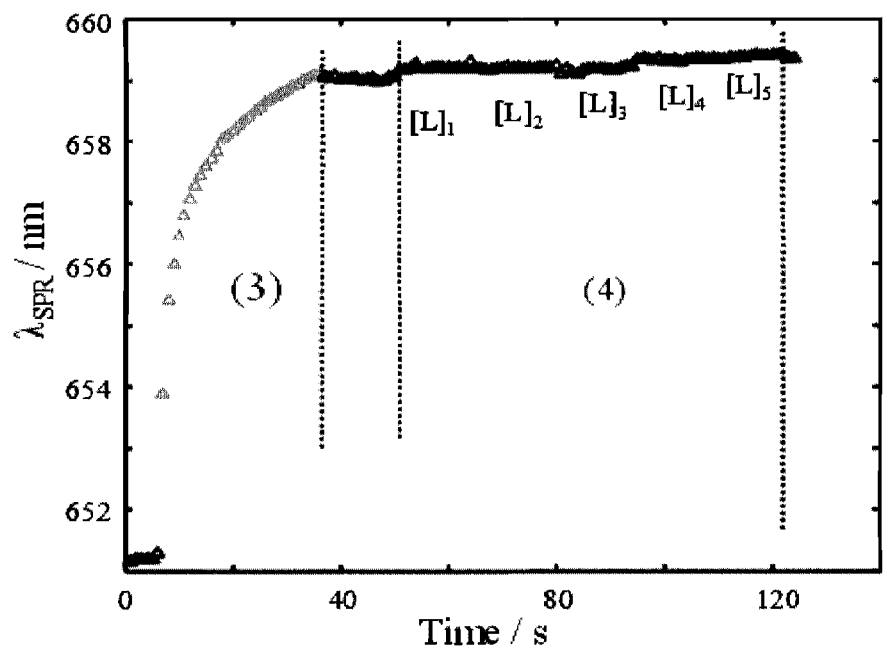
FIG. 10B shows a SPR sensorgram of hDHFR functionalized (step 3) sensor (nonspecific to peptidic ligand) exposed to increasing concentrations of EP80317 (step 4)

SPR Characterization of CD36 Ligands as Potential Therapeutic Agents of Interest Typically, unamplified SPR techniques do not yield large SPR response for molecules of less than 1000 g/mol, complicating the measurement of interactions between proteins and small molecules. This is the case of the CD36-ligand system investigated herein, where the ligands are small peptides of about 800 to 1000 g/mol. Indeed, according to the aforementioned principle, the binding of the small peptides to the CD36 receptor should be close to the limit of detection, thus providing unreliable affinity measurements. Nevertheless, a large shift in the signal was observed when exposing a CD36-His-tag-functionalized surface to increasing concentrations ($[L]_1<[L]_2<[L]_3<[L]_4<[L]_5$) of small peptide ligands, EP80317 (L) (FIG. 10A). This could be a consequence of a large conformational change of the CD36 receptor upon binding of specific ligands, thus providing the amplification sufficient for SPR signal detection. The blank assay (FIG. 10B), showing no significant change of signal for a hDHFR-His-Tag functionalized sensor exposed to the same peptide indicates that the change of signal observed with the CD36 surface is due to specific interactions between CD36 and its peptidic ligands.

Figure 11:
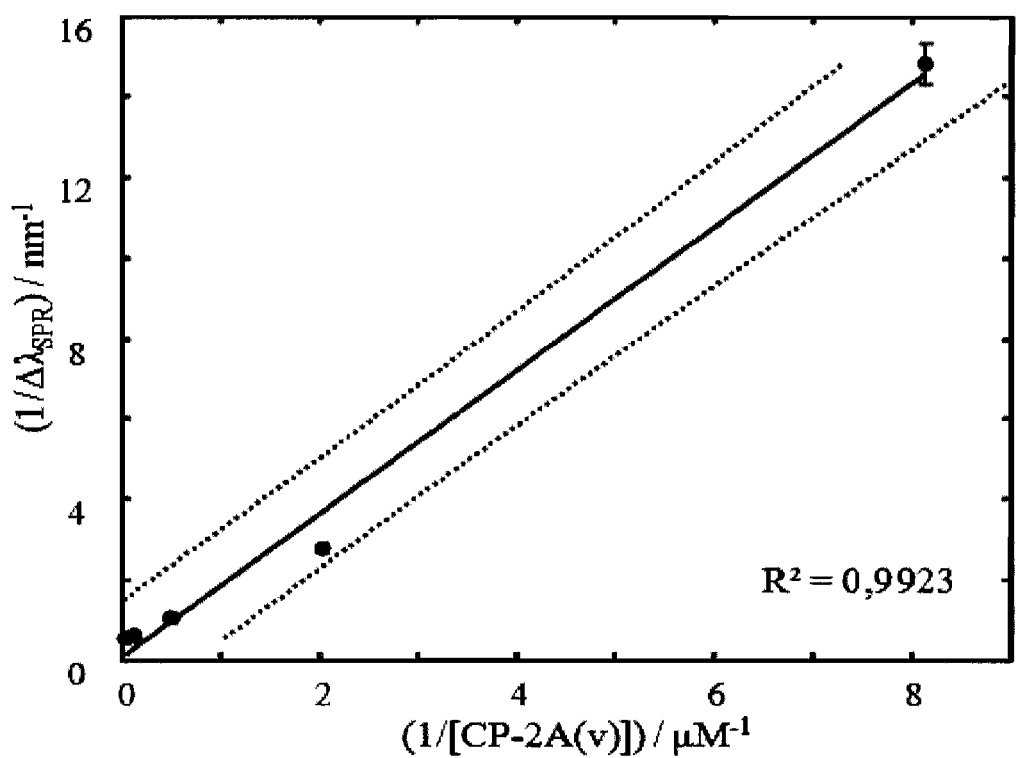
FIG. 11 shows a linear Langmuir plot for CP-2A(v) interacting with CD36 functionalized sensor. The error bars represent two standard deviations from the mean (the error bar is smaller than the data point for some measurements) and the dotted line represents two standard deviations from the linear least square regression.

The SPR setup was used for investigating the structure-activity relationships of various CD36 peptidic ligands. FIG. 11 shows a typical linear Langmuir plot for the ligand CP-2A (v) allowing the determination of $K_D$ for the CD36-ligand system. The measured $K_D$'s were compared to the $EC_{50}$ values obtained in the activated src-kinase assay following CD36 receptor activation by the tested peptides. Table III shows a good correlation between the $K_D$'s measured by SPR and the $EC_{50}$ for the activation of src-kinases. For the src-kinase cellular assay, the response sensitivity ($EC_{50}$) for the tested peptides (in decreasing order) was as follows: EP80317>CP-2A(v)>CP-3(iv)>DBG-178(27)>CP-2B(i). With SPR, the binding affinity to CD36, in decreasing order, was: DBG-178(27)>CP-2A(v)>EP80317>CP-3(iv)>CP-2B (i). CP-2B(i) featuring a low binding affinity to CD36 was used as a negative control for both methods indicating weak interactions with CD36. For CD36-peptidic ligands, a correlation appears between the affinity binding of the small peptides for CD36 as determined by SPR and their efficiency to produce a cellular response in the src kinase assay. Thus, SPR appears as a selective and sensitive method to screen for CD36 ligands.

TABLE III $EC_{50}$ values for CD36-peptidic ligands obtained using common techniques and corresponding $K_D$ values obtained using SPR.

| Ligands | SRC-kinase cellular assay EC50 (M) | SPR $K_D$ (M) |
|---|---|---|
| EP80317 | 2.6E−08 | 8.2E−08 |
| CP-2B(i) | >>10$^-$5 | 1.4E−06 |
| CP-3(iv) | 4.4E−08 | 3.8E−07 |
| CP-2A(v) | 2.6E−08 | 4.4E−08 |
| DBG-178$_{(27)}$ | 6.3E−08 | 2.2E−08 |

Therefore, peptide monolayers can be tailored for the immobilization of His-tagged biomolecules on an ultralow fouling surface. Peptide-based surfaces demonstrated their great potential to immobilize active proteins or enzymes when functionalized with NTA-type molecules. This enabled attachment of copper ion able to chelate His-tagged proteins commonly produced for their convenient purification. hDHFR-specific sensors were produced and regenerated using histidine, EDTA or imidazole without loss of hDHFR activity. Ligand screening may be performed rapidly, with reliability and simplicity. An affinity biosensor allowed the determination of relevant dissociation constants using the linear Langmuir equation. This strategy was successfully applied to determine the binding affinity of five peptidic ligands (GHRPs derivatives) to CD36 scavenger receptor, offering a potential tool for the screening of other synthetic ligands for this receptor.

Example 13

Attachment of Peptides on BK7 Glass Microscope Slides

The peptide immobilized in this protocol was: ($H_2N$)-G-$H_3$-$D_2$-OH, which was confirmed by mass spectrometry. The thiolated peptides previously used were coupled with 3-mercaptopropionic acid (3-MPA) allowing the formation of a covalent bound between Gold and sulphur. The addition of one glycine residue was done to provide better mobility to the N-terminal of the peptide enabling a good attachment to the NHS functionalized monolayer. BK7 microscope slides 22 mm×22 mm were previously washed in Piranha solution (mixture of 75% sulfuric acid ($H_2SO_4$) and 25% hydrogen peroxide ($H_2O_2$)) followed by water/hydrogen peroxide/ammonium hydroxide solution (in a 5:1:1 ratio) to increase the presence of silanol groups at the surface of BK7. For the carboxylation of the BK7 surface, clean microscope slides were immersed in a 0.2% solution of (3-aminopropyl)trimethoxysilane overnight, rinsed with ethanol and dried.

Figure 12:
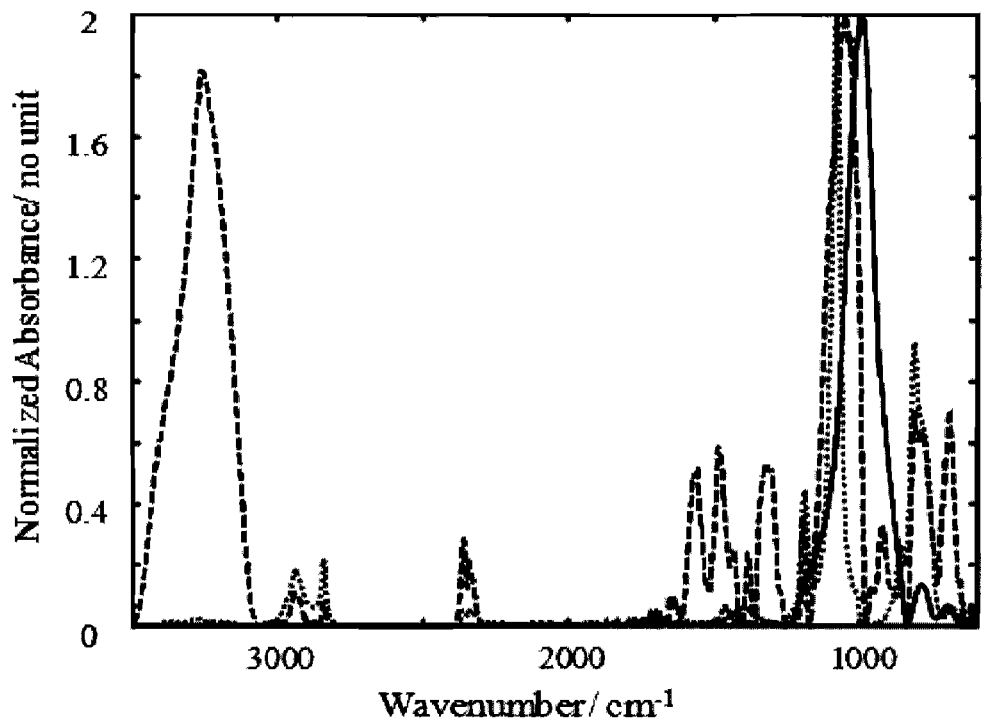
FIG. 12 shows the verification of attachment of silane on BK7. Solid line=BK7; dotted line=(3-aminopropyl)trimethoxysilane; and dashed line=Silane functionalized surface.

FIG. 12 shows the formation of an organic layer over BK7 made of (3-aminopropyl)trimethoxysilane. The Si—C stretch generated a strong absorption band visible at 1050 $cm^{-1}$ after functionalizing the surface. The absorption band at 1190 $cm^{-1}$ also appears indicating the vibration of the Si—O—C stretch for the functionalized surface and pure (3-aminopropyl)trimethoxysilane. The presence of a large absorption band at 3450 $cm^{-1}$ and a medium intensity absorption band at 2840 $cm^{-1}$ indicate respectively the N—H stretch and the C—H stretch of a primary amine essential to the following functionalization.

A 25 mM solution of potassium citrate was produced in 100 mM MES buffer at pH=5.00. 3 molar equivalent of N-hydroxysuccinimide (NHS) and 6 molar equivalent of N-dimethylaminopropyl-N'-ethylcarbodiimide hydrochloride (EDC) were dissolved in this solution immediately before immersing the slides in this solution overnight.

Figure 13:
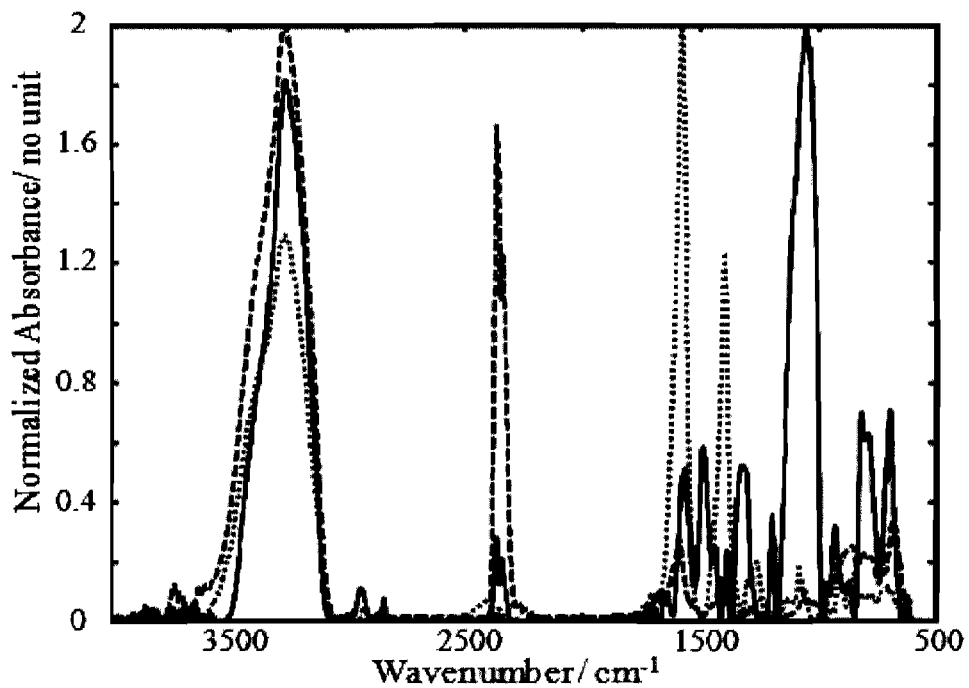
FIG. 13 shows the verification of attachment of citrate on silane functionalized surface. Solid line=BK7; dotted line=Citrate; and dashed line=Citrate functionalized surface.

The slides were rinsed with ethanol and dried before their IR spectrum was acquired to verify the formation of the citrate functionalized surface as shown in FIG. 13. The C═O stretch due to the formation of an amide bound is only visible for the citrate functionalized surface at 1680 $cm^{-1}$ indicating the attachment of citrate at the primary amine ending of (3-aminopropyl)trimethoxysilane. The broad band at 3450 $cm^{-1}$ is blue shifted while compared to the surface nonfunctionalized with citrate. This is due to the strong presence of OH stretch on the carboxylic acid functional groups of citrate.

Figure 14:
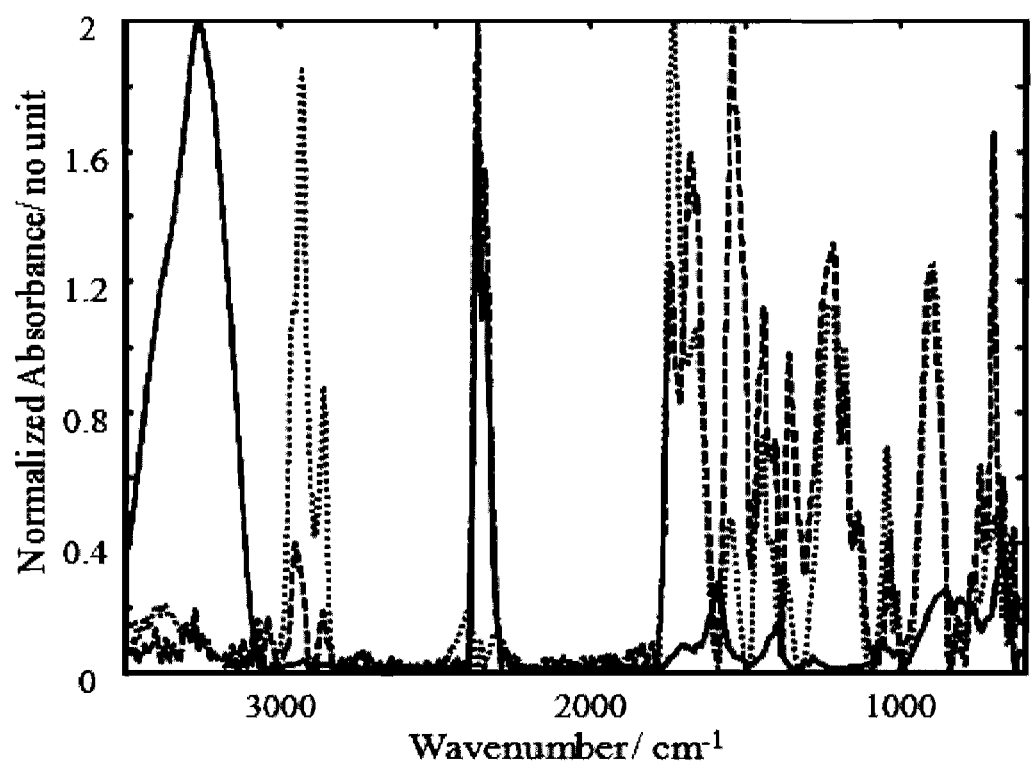
FIG. 14 shows the verification of attachment of peptides on citrate functionalized surface. Solid line=Citrate functionalized surface, dotted line=Peptide and dashed line=Peptide functionalized surface.

For the peptide attachment to the carboxylated BK7 surface, the slides were immersed for 20 minutes in a 50 mM:10 mM EDC/NHS solution in MES buffer. The slides were then rinsed with ethanol and dried to verify the attachment of the peptide on the surface as shown in FIG. 14. An important increase of the amide I band at 1645 $cm^{-1}$ indicates the presence of the peptide in α-helix on top of the surface. The amide III band due to the presence of C—N stretch of the peptide backbone is visible at 1440 cm-1. The presence of a strong absorption band at 1720 cm-1 indicated the presence of a C═O stretch characteristic to the C-terminal of the peptides.

Although the present invention has been described hereinabove by way of specific embodiments thereof, it can be modified, without departing from the spirit and nature of the subject invention as defined in the appended claims. In the claims, the word "comprising" is used as an open-ended term, substantially equivalent to the phrase "including, but not limited to". The singular forms "a", "an" and "the" include corresponding plural references unless the context clearly dictates otherwise.

What is claimed is:

1. A substrate comprising:
   a solid support for biosensing applications; and
   a heteropeptide attached to said support, wherein said heteropeptide is SSSDD (SEQ ID NO:10), HHHDD (SEQ ID NO:11), LLLDD (SEQ ID NO:12), LLLSS (SEQ ID NO:13), LLLHH (SEQ ID NO:14), HHHSS (SEQ ID NO:15), DDDHH (SEQ ID NO:16), DDDSS (SEQ ID NO:17), SSSHH (SEQ ID NO:18), LHDLHD (SEQ ID NO: 35), SHDSHD (SEQ ID NO: 34) or DSDSD (SEQ ID NO:32).

2. The substrate of claim 1, wherein said heteropeptide is SSSDD (SEQ ID NO:10), HHHDD (SEQ ID NO:11), LLLDD (SEQ ID NO:12), LLLSS (SEQ ID NO:13), LLLHH (SEQ ID NO:14), HHHSS (SEQ ID NO:15), DDDHH (SEQ ID NO:16), DDDSS (SEQ ID NO:17) or SSSHH (SEQ ID NO:18).

3. The substrate of claim 1, wherein said heteropeptide is LHDLHD (SEQ ID NO: 35) or SHDSHD (SEQ ID NO: 34).

4. The substrate of claim 1, wherein said heteropeptide is DSDSD (SEQ ID NO:32).

5. A method for reducing nonspecific adsorption on a solid support for biosensing applications comprising contacting said support with a heteropeptide wherein said heteropeptide is SSSDD (SEQ ID NO:10), HHHDD (SEQ ID NO:11), LLLDD (SEQ ID NO:12), LLLSS (SEQ ID NO:13), LLLHH (SEQ ID NO:14), HHHSS (SEQ ID NO:15), DDDHH (SEQ ID NO:16), DDDSS (SEQ ID NO:17), SSSHH (SEQ ID NO:18), LHDLHD (SEQ ID NO: 35), SHDSHD (SEQ ID NO: 34) or DSDSD (SEQ ID NO:32) under conditions permitting binding of said peptide to said support.

6. The substrate of claim 3, wherein said heteropeptide is LHDLHD (SEQ ID NO: 35).

7. The substrate of claim 3, wherein said heteropeptide is SHDSHD (SEQ ID NO: 34).

8. The substrate of claim 2, wherein said heteropeptide is SSSDD (SEQ ID NO:10).

9. The substrate of claim 1, wherein said heteropeptide is attached to said solid support through an N-terminal 3-mercaptoproprionic acid (3-MPA) linker.

10. The substrate of claim 1, wherein said heteropeptide is attached directly to said solid support.

11. The substrate of claim 1, wherein said solid support is a glass solid support.

12. The substrate of claim 1, wherein said substrate is a surface plasmon resonance (SPR) biosensor chip.

* * * * *